US010493165B2

(12) United States Patent
Selaru et al.

(10) Patent No.: US 10,493,165 B2
(45) Date of Patent: Dec. 3, 2019

(54) EXTRACELLULAR VESICLES FOR AGENT DELIVERY

(71) Applicant: THE JOHNS HOPKINS UNIVERSITY, Baltimore, MD (US)

(72) Inventors: Florin M. Selaru, Baltimore, MD (US); Ling Li, Baltimore, MD (US); Stephen J. Gould, Baltimore, MD (US)

(73) Assignee: THE JOHNS HOPKINS UNIVERSITY, Baltimore, MD (US)

( * ) Notice: Subject to any disclaimer, the term of this patent is extended or adjusted under 35 U.S.C. 154(b) by 0 days.

(21) Appl. No.: 15/545,937

(22) PCT Filed: Jan. 29, 2016

(86) PCT No.: PCT/US2016/015791
§ 371 (c)(1),
(2) Date: Jul. 24, 2017

(87) PCT Pub. No.: WO2016/123556
PCT Pub. Date: Aug. 4, 2016

(65) Prior Publication Data
US 2018/0028687 A1 Feb. 1, 2018

Related U.S. Application Data

(60) Provisional application No. 62/109,764, filed on Jan. 30, 2015, provisional application No. 62/150,318, filed on Apr. 21, 2015.

(51) Int. Cl.
*C12N 15/11* (2006.01)
*A61K 48/00* (2006.01)
(Continued)

(52) U.S. Cl.
CPC ........ *A61K 48/0008* (2013.01); *A61K 9/1075* (2013.01); *A61K 31/685* (2013.01);
(Continued)

(58) Field of Classification Search
CPC . A61K 48/0008; A61K 48/0075; C12P 19/34; G01N 33/574
See application file for complete search history.

(56) References Cited

U.S. PATENT DOCUMENTS

| 8,987,224 B2 | 3/2015 | Yao et al. |
| 9,085,778 B2 | 7/2015 | Lotvall et al. |

(Continued)

FOREIGN PATENT DOCUMENTS

| WO | 2006133022 A2 | 12/2006 |
| WO | 2009015357 A1 | 1/2009 |

(Continued)

OTHER PUBLICATIONS

Josson et al. (Oncogene (2015), published online Jul. 28, 2014, vol. 34:2690-2699).*

(Continued)

*Primary Examiner* — Terra C Gibbs
(74) *Attorney, Agent, or Firm* — Melissa Hunter-Ensor; Jana E. Harris; Greenberg Traurig, LLP

(57) ABSTRACT

The present invention relates to the field of extracellular vesicles. More specifically, the present invention provides methods and compositions for using extracellular vesicles as a vector for nucleic acid treatment in vivo of various diseases. In a specific embodiment, the present invention provides an extracellular vesicle isolated from a cell comprising one or more microRNAs (miRNAs) that have been loaded ex vivo into the vesicle so that the miRNAs are present in a higher concentration than when measured in the same extracellular vesicle isolated directly from the cell. In another embodiment, the present invention provides a method for treating cholangiocarcinoma in a subject com- (Continued)

prising the step of administering to the subject a plurality of exosomes comprising miR-195.

28 Claims, 17 Drawing Sheets

Specification includes a Sequence Listing.

(51) Int. Cl.

| | |
|---|---|
| C07H 21/02 | (2006.01) |
| C07H 21/04 | (2006.01) |
| C12P 21/00 | (2006.01) |
| A61K 31/7105 | (2006.01) |
| C12P 1/00 | (2006.01) |
| A61K 9/107 | (2006.01) |
| A61K 31/685 | (2006.01) |
| A61K 31/704 | (2006.01) |
| A61K 33/24 | (2019.01) |
| A61K 45/06 | (2006.01) |
| C12P 19/34 | (2006.01) |
| G01N 33/574 | (2006.01) |
| A61K 47/69 | (2017.01) |
| A61K 35/13 | (2015.01) |
| A61K 35/33 | (2015.01) |
| A61P 25/00 | (2006.01) |
| C12N 15/113 | (2010.01) |
| A61K 33/243 | (2019.01) |
| A61K 9/50 | (2006.01) |

(52) U.S. Cl.
CPC ........ *A61K 31/704* (2013.01); *A61K 31/7105* (2013.01); *A61K 33/24* (2013.01); *A61K 33/243* (2019.01); *A61K 35/13* (2013.01); *A61K 35/33* (2013.01); *A61K 45/06* (2013.01); *A61K 47/6901* (2017.08); *A61K 48/0075* (2013.01); *A61K 48/0091* (2013.01); *A61P 25/00* (2018.01); *C12N 15/113* (2013.01); *C12P 1/00* (2013.01); *C12P 19/34* (2013.01); *C12P 21/00* (2013.01); *G01N 33/574* (2013.01); *G01N 33/57438* (2013.01); *A61K 9/5068* (2013.01); *C12N 2310/141* (2013.01); *C12N 2320/32* (2013.01)

(56) References Cited

U.S. PATENT DOCUMENTS

| | | | |
|---|---|---|---|
| 9,889,210 B2 | 2/2018 | Lotvall et al. | |
| 9,944,932 B2 | 4/2018 | Schaapveld et al. | |
| 2013/0005599 A1 | 1/2013 | Klass et al. | |
| 2014/0323551 A1 | 10/2014 | Chung et al. | |
| 2015/0024475 A1 | 1/2015 | Duffin et al. | |
| 2019/0111155 A1 | 4/2019 | Lotvall et al. | |

FOREIGN PATENT DOCUMENTS

| | | |
|---|---|---|
| WO | 2013/138427 A1 | 9/2013 |
| WO | 2013138427 A1 | 9/2013 |
| WO | 2015120150 A1 | 8/2015 |

OTHER PUBLICATIONS

Tomas et al. (Prostate Cancer Prostatic Dis. (2006) vol. 9:414-419).*
Josson et al. (Oncogene (2015), published online Jul. 28, 2014, vol. 34:2690-2699), including Supplmentary Figures 1 and 2.*
Elvira Donnarumma Doctorate Dissertation "Cancer-associated fibroblasts (CAFs) release exosomal microRNAs that dictate an aggressive phenotype in breast cancer cells", deposit date Apr. 14, 2015.*
International Search Report and Written Opinion cited in corresponding PCT/US2016/015791, dated Apr. 8, 2016 (17 pages).
Li et al., "Human Bile Contains MicroRNA-Laden Extracellular Vesicles That Can Be Used for Cholangiocarcinoma Diagnosis", Hepatology, vol. 60, No. 3, Jul. 25, 2014, pp. 896-907.
Li et al., "Extracellular Vesicles Carry MicroRNA-195 to Intrahepatic Cholangiocarcinoma and Improve Survival in a Rat Model", Hepatology, vol. 65, No. 2, Feb. 1, 2017, pp. 500-514.
Supplementary European Search Report for corresponding European Application No. 16744228.4, dated Aug. 2, 2018 (11 pages).
Fang et al., "Higher-order oligomerization targets plasma membrane proteins and HIV gag to exosomes," PLoS Biology, Jun. 5, 2007 (Mar. 5, 2007), vol. 5, pp. 1-17.
Webber et al., "Cancer exosomes trigger fibroblast to myofibroblast differentiation," Cancer Research, Dec. 1, 2010 (Dec. 1, 2010), vol. 70, pp. 9621-9630.
Pupa et al., "New insights into the role of extracellular matrix during tumor onset and progression," Journal of Cellular Physiology, Sep. 1, 2002 (Sep. 1, 2002), vol. 192, pp. 259-267.
Fang et al., "Higher-order Oligomerization Targets Plasma Membrane Proteins and HIV Gag to Exosomes", PLoS Biology, Jun. 5, 2007, vol. 5, pp. 1-17.
Pupa et al., "New Insights into the Role of Extracellular Matrix During Tumor Onset and Progression", Journal of Cellular Physiology, Sep. 1, 2002, vol. 192, pp. 259-267.
Webber et al., "Cancer Exosomes Trigger Fibroblast to Myofibroblast Differentiation", Cancer Research, Dec. 1, 2010, vol. 70, pp. 9621-9630.
Communication to Article 94(3) EPC for corresponding European Patent Application No. 16744228.4, dated Jul. 16, 2019 (6 pages).

* cited by examiner

|  | LX2 CULTURED ALONE | | | LX2 CO-CULTURED WITH HuCCT1 | | | |
| --- | --- | --- | --- | --- | --- | --- | --- |
| DETECTOR | CT | QUANTITY | NORM TO U6 | CT | QUANTITY | NORM TO U6 | RATIO F/CAFs |
| miR-195 | 31.5 | 3.1 | 23.9 | 33.3 | 0.8 | 11.8 | 2 |
| miR-192 | 30.8 | 5.0 | 38.6 | 35.1 | 0.2 | 3.4 | 11 |
| miR-126 | 27.2 | 61.2 | 472.5 | 34.3 | 0.4 | 5.9 | 79 |

FIG. 2

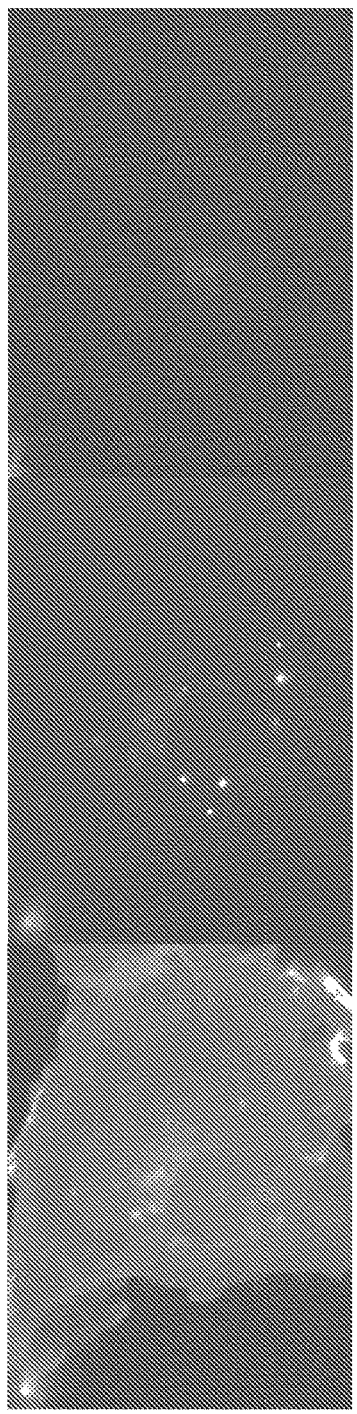

SEQUENCE LISTING

```
<160> NUMBER OF SEQ ID NOS: 5

<210> SEQ ID NO 1
<211> LENGTH: 87
<212> TYPE: DNA
<213> ORGANISM: Homo sapiens

<400> SEQUENCE: 1
agcttccctg gctctagcag cacagaaata ttggcacagg gaagcgagtc tgccaatatt    60
ggctgtgctg ctccaggcag ggtggtg                                        87

<210> SEQ ID NO 2
<211> LENGTH: 110
<212> TYPE: DNA
<213> ORGANISM: Homo sapiens

<400> SEQUENCE: 2
gccgagaccg agtgcacagg gctctgacct atgaattgac agccagtgct ctcgtctccc    60
ctctggctgc caattccata ggtcacaggt atgttcgcct caatgccagc                110

<210> SEQ ID NO 3
<211> LENGTH: 85
<212> TYPE: DNA
<213> ORGANISM: Homo sapiens

<400> SEQUENCE: 3
cgctggcgac gggacattat tactttggt acgcgctgtg acacttcaaa ctcgtaccgt     60
gagtaataat gcgccgtcca cggca                                          85

<210> SEQ ID NO 4
<211> LENGTH: 6
<212> TYPE: PRT
<213> ORGANISM: Artificial Sequence
```

```
<220> FEATURE:
<223> OTHER INFORMATION: Description of Artificial Sequence: Synthetic
      6xHis tag

<400> SEQUENCE: 4

His His His His His His
1               5

<210> SEQ ID NO 5
<211> LENGTH: 111
<212> TYPE: DNA
<213> ORGANISM: Homo sapiens

<400> SEQUENCE: 5
agacgccacg cctccgctgg cgacgggaca ttattacttt tggtacgcgc tgtgacactt      60
caaactcgta ccgtgagtaa taatgcgccg tccacggcac cgcatcgaaa a              111
```

EXTRACELLULAR VESICLES FOR AGENT DELIVERY

CROSS REFERENCE TO RELATED APPLICATIONS

This application is the U.S. national phase application, pursuant to 35 U.S.C. § 371, of PCT International Application Ser. No.: PCT/US2016/015791, filed Jan. 29, 2016, designating the United States and published in English, which claims priority to and the benefit of U.S Provisional Application No. 62/109,764, filed Jan. 30, 2015, and U.S. Provisional Application No. 62/150,318, filed Apr. 21, 2015, each of which are incorporated herein by reference in their entirety.

SEQUENCE LISTING

The instant application contains a Sequence Listing which has been filed electronically in ASCII format and is hereby incorporated by reference in its entirety. Said ASCII copy, created on Oct. 5, 2018, is named 167689_011203_U.S._S-L.txt and is 1,452 bytes in size.

FIELD OF THE INVENTION

The present invention relates to the field of extracellular vesicles (e.g., exosomes, microvesicles, macrovesicles). More specifically, the present invention provides compositions comprising extracellular vesicles for delivery of agents (e.g., polynucleotides, polypeptides, small molecules) and methods of using such compositions, for example, in therapeutic, imaging, and research methods.

BACKGROUND OF THE INVENTION

Cholangiocarcinoma (CCA) is the second most common primary liver cancer in the United States. The survival of CCA patients is dismal, usually measured in months. Primary therapy with surgery is applicable to fewer than 20% of patients. Photodynamic therapy and chemotherapy provide responses in a minority of patients without curative intent. Thus there is an urgent need for improved treatment for CCA, and novel treatment modalities for CCA are potentially translatable to other types of cancer. In addition, there exists a need for methods that selectively deliver therapeutics to cancer cells. Such compositions and methods could be translated to a wide array of disease treatments.

SUMMARY OF THE INVENTION

The present invention provides extracellular vesicles (EVs) derived from a cancer associated cell (e.g., fibroblast-like cell, stromal cell) comprising an agent (e.g., polypeptide, polynucleotide, small molecule), and methods of using such EVs to deliver the agent to a target cell.

The invention generally provides an extracellular vesicle isolated from a cancer associated fibroblast (CAF), where the vesicle contains an exogenous agent.

In one aspect, the invention provides an extracellular vesicle isolated from a cancer associated fibroblast (CAF), where the vesicle contains a heterologous polynucleotide identified as being down-regulated in the CAF, and where the extracellular vesicle selectively targets a cancer cell.

In various embodiments of the above-aspects or any other aspect of the invention delineated herein, the agent is an exogenous polynucleotide. In various embodiments of the above-aspects the polynucleotide is miR-195, miR-126, or miR-192 or is a polynucleotide encoding miR-195, miR-126, or miR-192. In various embodiments of the above-aspects the polynucleotide is a vector encoding miR-195, miR-126, or miR-192. In various embodiments of the above-aspects, the polypeptide is a recombinant polypeptide heterologously expressed in the CAF or loaded into the cell or extracellular vesicle ex vivo. In various embodiments of the above-aspects, the polynucleotide is a recombinant polynucleotide that is heterologously expressed in the cell or is loaded into the cell ex vivo. In various embodiments of the above-aspects, the recombinant polynucleotide is a microRNA. In various embodiments of the above-aspects the microRNA is miR-195, miR-126, or miR-192. In various embodiments of the above-aspects, the small molecule is a lipid or other hydrophobic small molecule. In various embodiments of the above-aspects, the small molecule is doxorubicin, cisplatin, or phosphatidyl ethanolamine. In various embodiments of the above-aspects, the phosphatidyl ethanolamine is derivatized with an agent selected from the group consisting of rhodamine, fluorescein, biotin, streptavidin, a small molecule, a polynucleotide, and a polypeptide. In various embodiments of the above-aspects, the polypeptide is an antibody, a polypeptide that localizes to a specific cell type, a therapeutic protein, or protein that can be used for imaging purposes. In various embodiments of the above-aspects, the agent is a nanoparticle, paramagnetic particle, microsphere, or nanosphere for magnetic imaging. In various embodiments of the above-aspects, the cancer associated fibroblast is a stromal cell. In various embodiments of the above-aspects, the stromal cell is derived from a tumor microenvironment. In various embodiments of the above-aspects, the tumor is a cholangiocarcinoma, hepatocellular carcinoma, or hepatoma. In various embodiments of the above-aspects, the tumor is a breast cancer tumor, pancreatic tumor, glioblastoma, melanoma, lung cancer tumor, ovarian cancer tumor, or any other type of cancer. In various embodiments of the above-aspects, the extracellular vesicle is isolated from a bodily fluid selected from the group consisting of blood, plasma, serum, urine, stool, semen, cerebrospinal fluid, prostate fluid, lymphatic drainage, bile fluid, and pancreatic secretions. In various embodiments of the above-aspects, the extracellular vesicle is isolated from cell culture media. In various embodiments of the above-aspects, the extracellular vesicle is isolated from cells cultured in conditioned media obtained from a culture containing cancer cells. In various embodiments of the above-aspects, the extracellular vesicle is isolated from a culture containing a CAF derived from a fibroblast, fibroblast-like cell, stellate cell, or myofibroblast. In various embodiments of the above-aspects, the CAF expresses one or more of alpha smooth muscle actin and/or collagen. In various embodiments of the above-aspects, the fibroblast-like cell has a fibroblast morphology. In various embodiments of the above-aspects, the vesicle expresses increased levels of one or more markers selected from the group consisting of alpha-SMA, Collagen, Vimentin (FSP-1), S100, Metalloproteinases, NG2, PDGFR-B, SDF1/CXCL12, CD34, Fibroblast activation protein (FAP), FSP-1, CD31, Thy-1, and Gremlin. In various embodiments of the above-aspects, the vesicle expresses reduced levels of laminin. In various embodiments of the above-aspects, the CAF is derived from a fibroblast cultured for at least 1-14 days in the presence of a cancer cell or in the presence of conditioned media derived from a cancer cell culture. In various embodiments of the above-aspects, the vesicle is isolated from mammalian cells.

In various embodiments of the above-aspects, the vesicle is an exosome or a microvesicle.

In another aspect, the invention provides a method for obtaining an extracellular vesicle, the method involving culturing a fibroblast or stromal cell in conditioned media obtained from a cancer cell culture, and isolating extracellular vesicles from the media.

In another aspect, the invention provides an extracellular vesicle produced according to the method of the above aspects.

In another aspect, the invention provides a pharmaceutical composition containing a vesicle of any of the above aspects.

In another aspect, the invention provides a method of delivering an agent to a cell, the method involving contacting the cell with a vesicle of any of the above-aspects, thereby delivering the agent to the cell.

In another aspect, the invention provides a method of reducing a tumor in a subject, the method involving contacting the cell with the vesicle of any of the above aspects.

In another aspect, the invention provides a method of altering gene expression in a cell, the method involving contacting the cell with a vesicle of any previous aspect.

In another aspect, the invention provides a method for treating cancer in a subject comprising administering to the subject a pharmaceutical composition comprising an effective amount of the vesicle of any previous aspect.

In another aspect, the invention provides a method for treating cholangiocarcinoma, hepatocellular carcinoma, or hepatoma in a subject comprising administering to the subject a pharmaceutical composition comprising an effective amount of an extracellular vesicle isolated from a CAF over-expressing a recombinant polynucleotide encoding miR-195, miR-192, or miR-126.

In another aspect, the invention provides a pharmaceutical composition comprising a first and a second extracellular vesicle, where each vesicle contains a different agent. In one embodiment, each vesicle comprises a different miRNA.

In another aspect, the invention provides a pharmaceutical composition comprising a plurality of exosomes, where each exosome contains one of miR-195, miR-192, or miR-126.

In another aspect, the invention provides a composition for imaging studies, the composition comprising an extracellular vesicle isolated from a cancer associated fibroblast (CAF) or fibroblast-like cell, where the vesicle contains a detectable agent. In one embodiment, the detectable agent is an imaging agent. In another embodiment, the imaging agent is a nanoparticle, magnetite, nanoparticle, paramagnetic particle, microsphere, nanosphere, and is selectively targeted to cancer cells.

In another aspect, the invention provides a kit for delivering an agent to a cell the kit comprising an extracellular vesicle isolated from a cancer associated fibroblast (CAF) or fibroblast-like cell, where the vesicle contains an agent.

In various embodiments of the above-aspects, the method inhibits tumor cell proliferation. In various embodiments of the above-aspects, the extracellular vesicle is an exosome. In various embodiments of the above-aspects, the cancer cells are derived from a liver cancer or breast cancer. In various embodiments of the above-aspects, the cell is cultured for between about 3-days and 2 weeks in conditioned media. In various embodiments of the above-aspects, the method further contains incubating the isolated extracellular vesicle in a solution comprising an agent. In various embodiments of the above-aspects, the extracellular vesicle is incubated for between about 1 and 4 hours. In various embodiments of the above-aspects, the fibroblast or stromal cell contains a vector encoding a recombinant protein or microRNA. In various embodiments of the above-aspects, the extracellular vesicle contains an increased level of a recombinant protein, polynucleotide, or small molecule than a corresponding control cell not cultured in conditioned media. In various embodiments of the above-aspects, the extracellular vesicle is a microvesicle.

DEFINITIONS

Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them below, unless specified otherwise.

By "cancer associated fibroblast (CAF)" is meant a fibroblast that expresses increased levels of alpha-smooth muscle actin (SMA), PDGFRbeta, and/or collagen relative to a control fibroblast. In one embodiment, a CAF expresses at least about 2-fold, 5-fold, 10-fold more alpha-SMA, PDGFRbeta, and collagen relative to a non-CAF fibroblast (i.e., a fibroblast derived from healthy non-cancerous tissue, or that has not been cultured in conditioned media derived from cancer cells). A CAF derived EV promotes tumor growth and metastasis. In contrast, CAFs of the invention comprise agents that inhibit tumor growth. In another embodiment, a CAF expresses reduced levels of miR-195, miR-192 and miR-126 relative to a reference. In another embodiment, a CAF overexpresses any one or more of the following markers: Actin (a-SMA), Collagen, Vimentin (FSP-1), S100, Metalloproteinases, NG2, PDGFR-B, SDF1 (CXCL12), CD34, Fibroblast activation protein (FAP) and FSP-1 (as well as CD31), Thy-1, and Gremlin relative to a reference. In another embodiment, a CAF expresses reduced levels of laminin relative to a reference. In addition to stromal cells, CAFs may be derived from cells having proximity to the tumor in vivo. Thus, CAFs may be derived from cells associated with blood vessels or local deposits of fat near the term. In some instances, a CAF is identified at a site distant from the tumor. Such CAFs are identified as CAFs or their subtypes by marking studies. In particular embodiments, a cancer associated cell (CAC) may be used in place of a CAF. CACs include brain derived glia, oligodendroglia, and microglia. Other CACs include Breast-EMT and bone marrow stem cells which have become CAFs. Other cells useful in the invention include reactive cell populations associated with cancer that express in various proportions FSP-1, S100, Metalloproteinases, NG2 a-SMA, and PDGFR-B.

As used herein, the term "microRNA," "miRNA," or "miR" refers to RNAs that function post-transcriptionally to regulator expression of genes, usually typically by binding to complementary sequences in the three prime (3') untranslated regions (3' UTRs) of target messenger RNA (mRNA) transcripts, usually resulting in gene silencing. miRNAs are typically small regulatory RNA molecules, for example, 21 or 22 nucleotides long. The terms "microRNA," "miRNA," and "miR" are used interchangeably.

By "miR-195" is meant a polynucleotide or fragment thereof having at least about 85% or greater nucleic acid sequence identity to the polynucleotide sequence provided at NCBI Accession No. NR_029712 that is capable of modulating gene expression. In one embodiment, the miRNA affects the stability and/or translation of mRNAs.

An exemplary miR-195 nucleic acid sequence is provided below: Homo sapiens miR-195

```
                                                    (SEQ ID NO: 1)
  1 agcttccctg gctctagcag cacagaaata ttggcacagg gaagcgagtc tgccaatatt 61 ggctgtgctg ctccaggcag ggtggtg
```

The exemplary sequence represents the predicted microRNA stem-loop. Some sequence at the 5' and 3' ends may not be included in the intermediate precursor miRNA produced by Drosha cleavage.

By "miR-195 gene" is meant the polynucleotide sequence encoding the miR-195 miRNA.

By "miR-192" is meant a polynucleotide or fragment there of having at least about 85% or greater identity to the polynucleotide sequence provided at NCBI Accession No. NR_029578 that is capable of modulating gene expression. In one embodiment, the miRNA affects the stability and/or translation of mRNAs. An exemplary miR-192 nucleotide sequence is provided below: Homo sapiens miR-192

```
                                                    (SEQ ID NO: 2)
  1 gccgagaccg agtgcacagg gctctgacct atgaattgac agccagtgct ctcgtctccc 61 ctctggctgc caattccata ggtcacaggt atgttcgcct caatgccagc
```

The exemplary sequence represents the predicted microRNA stem-loop. Some sequence at the 5' and 3' ends may not be included in the intermediate precursor miRNA produced by Drosha cleavage.

By "miR-192 gene" is meant the polynucleotide sequence encoding the miR-192 miRNA.

By "miR-126" is meant a polynucleotide or fragment there of having at least about 85% or greater identity to the polynucleotide sequence provided at NCBI Accession No. NR_029695 that is capable of modulating gene expression. In one embodiment, the miRNA affects the stability and/or translation of mRNAs. An exemplary miR-126 nucleotide sequence is provided below: Homo sapiens miR-126

```
                                                    (SEQ ID NO: 3)
  1 cgctggcgac gggacattat tacttttggt acgcgctgtg acacttcaaa ctcgtaccgt 61 gagtaataat gcgccgtcca cggca
```

The exemplary sequence represents the predicted microRNA stem-loop. Some sequence at the 5' and 3' ends may not be included in the intermediate precursor miRNA produced by Drosha cleavage.

By "miR-126 gene" is meant the polynucleotide sequence encoding the miR-126 miRNA.

By "agent" is meant a polypeptide, polynucleotide, or fragment, or analog thereof, small molecule, or other biologically active molecule.

By "alteration" is meant a change (increase or decrease) in the expression levels of a gene or polypeptide as detected by standard art known methods such as those described above. As used herein, an alteration includes a 10% change in expression levels, preferably a 25% change, more preferably a 40% change, and most preferably a 50% or greater change in expression levels.

As used herein, the term "animal" refers to any member of the animal kingdom. The term "animal" may refer to humans at any stage of development or any non-human animal at any stage of development. In some embodiments, the term "animal" may refer to a transgenic or genetically engineered animal or a clone.

The term "antibody," as used herein, refers to an immunoglobulin molecule which specifically binds with an antigen. Methods of preparing antibodies are well known to those of ordinary skill in the science of immunology. Antibodies can be intact immunoglobulins derived from natural sources or from recombinant sources and can be immunoreactive portions of intact immunoglobulins. Antibodies are typically tetramers of immunoglobulin molecules. Tetramers may be naturally occurring or reconstructed from single chain antibodies or antibody fragments. Antibodies also include dimers that may be naturally occurring or constructed from single chain antibodies or antibody fragments. The antibodies in the present invention may exist in a variety of forms including, for example, polyclonal antibodies, monoclonal antibodies, Fv, Fab and F(ab') 2, as well as single chain antibodies (scFv), humanized antibodies, and human antibodies (Harlow et al., 1999, In: Using Antibodies: A Laboratory Manual, Cold Spring Harbor Laboratory Press, NY; Harlow et al., 1989, In: Antibodies: A Laboratory Manual, Cold Spring Harbor, N.Y.; Houston et al., 1988, Proc. Natl. Acad. Sci. USA 85:5879-5883; Bird et al., 1988, Science 242:423-426). In some embodiments, the antibody specifically binds to C4A polypeptide.

The term "antibody fragment" refers to a portion of an intact antibody and refers to the antigenic determining variable regions of an intact antibody. Examples of antibody fragments include, but are not limited to, Fab, Fab', F(ab') 2, and Fv fragments, linear antibodies, scFv antibodies, single-domain antibodies, such as camelid antibodies (Riechmann, 1999, Journal of Immunological Methods 231:25-38), composed of either a VL or a VH domain which exhibit sufficient affinity for the target, and multispecific antibodies formed from antibody fragments. The antibody fragment also includes a human antibody or a humanized antibody or a portion of a human antibody or a humanized antibody.

As used herein, the term "approximately" or "about," as applied to one or more values of interest, refers to a value that is similar to a stated reference value. In some embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction of the stated reference value unless otherwise stated or otherwise evident from the context.

By "control" is meant a standard or reference condition. The term "control" refers to a standard against which results are compared. In some embodiments, a control is used at the same time as a test variable or subject to provide a comparison. In some embodiments, a control is a historical control that has been performed previously, a result or amount that has been previously known, or an otherwise existing record. A control may be a positive or negative control.

By "decreases" is meant a reduction by at least about 5% relative to a reference level. A decrease may be by 5%, 10%, 15%, 20%, 25% or 50%, or even by as much as 75%, 85%, 95% or more.

By "an effective amount" is meant the amount of an agent required to ameliorate the symptoms of a disease relative to an untreated patient. In one embodiment, the disease is cancer (e.g., cholangiocarcinoma, hepatocellular carcinoma, hepatoma). In other embodiments, the disease is a single gene disorder including, but not limited to, cystic fibrosis, sickle cell anemia, Tay-Sachs disease, myotonic dystrophy, Duchenne muscular dystrophy, Fragile X syndrome, glycogen storage diseases, and spinal muscular atrophy. As would be appreciated by one of ordinary skill in the art, the exact amount required to treat a disease will vary from subject to subject, depending on age, general condition of the subject, the severity of the condition being treated, the particular compound and/or composition administered, and the like. The effective amount of active agent(s) used to practice the present invention for therapeutic treatment of a disease varies depending upon the manner of administration, the age, body weight, and general health of the subject. Ultimately, the attending physician or veterinarian will decide the appropriate amount and dosage regimen. Such amount is referred to as an "effective" amount.

By "exogenous" is meant foreign. An exogenous agent is one that is not naturally occurring in the cell, such as a protein that is recombinantly expressed.

As used herein, the term "exosome" refers to a small membrane extracellular vesicle of ~30-300 nm diameter that is secreted from producing cells into the extracellular environment, as described initially by Trams et al., 1981, BBA. The surface of an exosome comprises a lipid bilayer from the membrane of the donor cell, and the lumen of the exosome is topologically the same as the cytosol from the cell that produces the exosome. The exosome contains proteins, RNAs, lipids, and carbohydrates of the producing cell, though some may be modified or added to the exosome after its release from the cell, either through natural processes or by experimental manipulation.

By "fragment" is meant a portion (e.g., at least 10, 25, 50, 100, 125, 150, 200, 250, 300, 350, 400, or 500 amino acids or nucleic acids) of a protein or nucleic acid molecule that is substantially identical to a reference protein or nucleic acid and retains the biological activity of the reference.

By "heterologous" is meant originating in a different cell type or species from the recipient.

A "host cell" is any prokaryotic or eukaryotic cell that contains either a cloning vector or an expression vector. This term also includes those prokaryotic or eukaryotic cells that have been genetically engineered to contain the cloned gene(s) in the chromosome or genome of the host cell.

By "inhibits a neoplasia" is meant decreases the propensity of a cell to develop into a neoplasia or slows, decreases, or stabilizes the growth or proliferation of a neoplasia.

As used herein, the term "in vitro" refers to events or experiments that occur in an artificial environment, e.g., in a petri dish, test tube, cell culture, etc., rather than within a multicellular organism.

As used herein, the term "in vivo" refers to events or experiments that occur within a multicellular organism.

As used herein, the term "isolated" refers to a substance, molecule, or entity that has been either separated from at least some of the components with which it was associated when initially produced in nature or through an experiment, and/or produced, prepared, or manufactured by the hand of man. Isolated substances and/or entities may be separated from at least about 10%, about 20%, about 30%, about 40%, about 50%, about 60%, about 70%, about 80%, about 90%, about 95%, about 98%, about 99%, substantially 100%, or 100% of the other components with which they were initially associated. In some embodiments, isolated agents are more than about 80%, about 85%, about 90%, about 91%, about 92%, about 93%, about 94%, about 95%, about 96%, about 97%, about 98%, about 99%, substantially 100%, or 100% pure. As used herein, a substance is "pure" if it is substantially free of other components.

By "inhibitory nucleic acid molecule" is meant a single stranded or double-stranded RNA, siRNA (short interfering RNA), shRNA (short hairpin RNA), or antisense RNA, or a portion thereof, or an analog or mimetic thereof, that when administered to a mammalian cell results in a decrease (e.g., by 10%, 25%, 50%, 75%, or even 90-100%) in the expression of a target sequence. Such inhibitory nucleic acid molecules may delivered using compositions of the invention. Typically, a nucleic acid inhibitor comprises or corresponds to at least a portion of a target nucleic acid molecule, or an ortholog thereof, or comprises at least a portion of the complementary strand of a target nucleic acid molecule.

By "marker" is meant any protein or polynucleotide having an alteration in expression level or activity that is associated with a disease or disorder.

By "modification" is meant any biochemical or other synthetic alteration of a nucleotide, amino acid, or other agent relative to a naturally occurring reference agent.

By "neoplasia" is meant any disease that is caused by or results in inappropriately high levels of cell division, inappropriately low levels of apoptosis, or both. For example, cancer is a neoplasia. Examples of cancers include, without limitation, leukemias (e.g., acute leukemia, acute lymphocytic leukemia, acute myelocytic leukemia, acute myeloblastic leukemia, acute promyelocytic leukemia, acute myelomonocytic leukemia, acute monocytic leukemia, acute erythroleukemia, chronic leukemia, chronic myelocytic leukemia, chronic lymphocytic leukemia), polycythemia vera, lymphoma (Hodgkin's disease, non-Hodgkin's disease), Waldenstrom's macroglobulinemia, heavy chain disease, and solid tumors such as sarcomas and carcinomas (e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, cholangiocarcinoma (also termed bile duct carcinoma), choriocarcinoma, seminoma, embryonal carcinoma, Wilm's tumor, cervical cancer, uterine cancer, testicular cancer, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodenroglioma, schwannoma, meningioma, melanoma, neuroblastoma, and retinoblastoma). Lymphoproliferative disorders are also considered to be proliferative diseases.

In some embodiments, "cancer" can include histologic and molecular subtypes of liver cancer, pancreatic cancer, prostate cancer, breast cancer, hepatocellular carcinoma, colon cancer, lung cancer, lymphoma, leukemia, melanoma, basal cell cancer, cervical cancer, colorectal cancer, stomach cancer, bladder cancer, anal cancer, bone cancer, brain tumor, esophageal cancer, gall bladder cancer, gastric cancer, testicular cancer, Hodgkin Lymphoma, intraocular melanoma, kidney cancer, oral cancer, melanoma, neuroblastoma, Non-Hodgkin Lymphoma, ovarian cancer, retinoblastoma, skin cancer, throat cancer, and thyroid cancer. Fibroblasts having proximity to any of the aforementioned cancer types or grown in a culture comprising such cancer cells are CAFs. For example, breast cancer associated fibroblasts are those growing in a culture that also comprises a cancer cell.

Cholangiocarcinoma or hepatocellular cancer associated fibroblasts are those growing in a culture that also comprises a cancer cell.

As used herein, the term "microvesicle" refers to a single membrane vesicle secreted by cells that may have a larger diameter than those which some refer to as exosomes. Microvesicles may have a diameter (or largest dimension where the particle is not spheroid) of between about 10 nm to about 5000 nm (e.g., between about 50 nm and 1500 nm, between about 75 nm and 1500 nm, between about 75 nm and 1250 nm, between about 50 nm and 1250 nm, between about 30 nm and 1000 nm, between about 50 nm and 1000 nm, between about 100 nm and 1000 nm, between about 50 nm and 750 nm, etc.). Microvesicles suitable for use in the present invention originate from cells yet different subpopulations of microvesicles may exhibit different surface/lipid characteristics. Alternative names for microvesicles include, but are not limited to, exosomes, ectosomes, membrane particles, exosome-like particles, and apoptotic vesicles. As used herein, an abbreviated form "MV" is sometimes used to refer to microvesicle.

As used herein, the term "microvesicle" refers to a membranous particle comprising fragments of plasma membrane that is derived from various cell types. Typically, microvesicles have a diameter (or largest dimension where the particle is not spheroid) of between about 10 nm to about 5000 nm (e.g., between about 50 nm and 1500 nm, between about 75 nm and 1500 nm, between about 75 nm and 1250 nm, between about 50 nm and 1250 nm, between about 30 nm and 1000 nm, between about 50 nm and 1000 nm, between about 100 nm and 1000 nm, between about 50 nm and 750 nm, etc.). Typically, at least part of the membrane of the microvesicle is directly obtained from a cell (also known as a donor cell). Microvesicles suitable for use in the present invention may originate from cells by membrane inversion, exocytosis, shedding, blebbing, and/or budding. Depending on the manner of generation (e.g., membrane inversion, exocytosis, shedding, or budding), the microvesicles contemplated herein may exhibit different surface/lipid characteristics.

Alternative names for microvesicles include, but are not limited to, exosomes, ectosomses, membrane particles, exosome-like particles, and apoptotic vesicles. As used herein, an abbreviated form "MV" is sometimes used to refer to microvesicle.

As used herein, an individual "suffering from" a disease, disorder, or condition means that the person has been diagnosed with or displays one or more symptoms of the disease, disorder, or condition By "nucleic acid molecule" is meant an oligomer or polymer of ribonucleic acid or deoxyribonucleic acid, or analog thereof. This term includes oligomers consisting of naturally occurring bases, sugars, and intersugar (backbone) linkages as well as oligomers having non-naturally occurring portions which function similarly. Such modified or substituted oligonucleotides are often preferred over native forms because of properties such as, for example, enhanced stability in the presence of nucleases. In certain embodiments, the term "nucleic acid molecule" refers to genetic material that can be transferred via EVs including, but not limited to, miRNA, mRNA, tRNA, rRNA, siRNA, shRNA, DNA (including fragments, plasmids, and the like). Such genetic materials can be transferred to EVs via transfection, transformation, electroporation, and microinjection.

By "obtaining" as in "obtaining the inhibitory nucleic acid molecule" is meant synthesizing, purchasing, or otherwise acquiring the inhibitory nucleic acid molecule.

By "operably linked" is meant that a first polynucleotide is positioned adjacent to a second polynucleotide that directs transcription of the first polynucleotide when appropriate molecules (e.g., transcriptional activator proteins) are bound to the second polynucleotide.

By "positioned for expression" is meant that the polynucleotide of the invention (e.g., a DNA molecule) is positioned adjacent to a DNA sequence that directs transcription and translation of the sequence (i.e., facilitates the production of, for example, a recombinant microRNA molecule described herein).

By "portion" is meant a fragment of a polypeptide or nucleic acid molecule. This portion contains, preferably, at least 10%, 20%, 30%, 40%, 50%, 60%, 70%, 80%, or 90% of the entire length of the reference nucleic acid molecule or polypeptide. A fragment may contain 5, 6, 7, 8, 9, 10, 11, 12, 13, 14, 15, 16, 17, 18, 19, 20, or 21 nucleotides.

By "reference" is meant a standard or control condition.

By "reporter gene" is meant a gene encoding a polypeptide whose expression may be assayed; such polypeptides include, without limitation, glucuronidase (GUS), luciferase, chloramphenicol transacetylase (CAT), and beta-galactosidase.

By "selectively deliver" is meant that the majority of the EV is delivered to a targeted cell type relative to non-target cells present in the culture, tissue, or organ. In embodiments, greater than about 50%, 60%, 70%, 80%, 90%, 95% or even approaching 100% of the EVs are delivered to a desired cell type. In other embodiments, only about 10%, 15%, 20% 25%, 30%, 35%, or 40% of the EVs are delivered to non-target cells.

The term "siRNA" refers to small interfering RNA; a siRNA is a double stranded RNA that "corresponds" to or matches a reference or target gene sequence. This matching need not be perfect so long as each strand of the siRNA is capable of binding to at least a portion of the target sequence. SiRNA can be used to inhibit gene expression, see for example Bass, 2001, Nature, 411, 428 429; Elbashir et al., 2001, Nature, 411, 494 498; and Zamore et al., Cell 101:25-33 (2000).

"As used herein, the term "stromal cell" refers to non-vascular, non-inflammatory, non-epithelial connective tissue cells of any organ that surround a tumor. Stromal cells are also known as cancer-associated fibroblasts. Stromal cells support the function of the parenchymal cells of that organ. Fibroblasts and pericytes are among the most common types of stromal cells. The stromal cells can be derived from numerous body tissue types, including, but not limited to, breast tissue, thymic tissue, bone marrow tissue, bone tissue, dermal tissue, muscle tissue, respiratory tract tissue, gastrointestinal tract tissue, genitourinary tissue, central nervous system tissue, peripheral nervous system tissue, reproductive tract tissue.

As used herein, the term "subject" refers to a human or any non-human animal (e g, mouse, rat, rabbit, dog, cat, cattle, swine, sheep, horse or primate). A human includes pre and post natal forms. In many embodiments, a subject is a human being. A subject can be a patient, which refers to a human presenting to a medical provider for diagnosis or treatment of a disease. The term "subject" is used herein interchangeably with "individual" or "patient." A subject can be afflicted with or is susceptible to a disease or disorder but may or may not display symptoms of the disease or disorder. The term "pharmaceutically-acceptable excipient" as used herein means one or more compatible solid or liquid filler, diluents or encapsulating substances that are suitable for administration into a human.

By "specifically binds" is meant a molecule (e.g., peptide, polynucleotide) that recognizes and binds a protein or nucleic acid molecule of the invention, but which does not substantially recognize and bind other molecules in a sample, for example, a biological sample, which naturally includes a protein of the invention.

By "substantially identical" is meant a protein or nucleic acid molecule exhibiting at least 50% identity to a reference amino acid sequence (for example, any one of the amino acid sequences described herein) or nucleic acid sequence (for example, any one of the nucleic acid sequences described herein). Preferably, such a sequence is at least 60%, more preferably 80% or 85%, and still more preferably 90%, 95% or even 99% identical at the amino acid level or nucleic acid to the sequence used for comparison.

Sequence identity is typically measured using sequence analysis software (for example, Sequence Analysis Software Package of the Genetics Computer Group, University of Wisconsin Biotechnology Center, 1710 University Avenue, Madison, Wis. 53705, BLAST, BESTFIT, GAP, or PILEUP/PRETTYBOX programs). Such software matches identical or similar sequences by assigning degrees of homology to various substitutions, deletions, and/or other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine. In an exemplary approach to determining the degree of identity, a BLAST program may be used, with a probability score between $e^{-3}$ and $e^{-100}$ indicating a closely related sequence.

By "targets" is meant alters the biological activity of a target polypeptide or nucleic acid molecule.

By "transformed cell" is meant a cell into which (or into an ancestor of which) has been introduced, by means of recombinant DNA techniques, a polynucleotide molecule encoding (as used herein) a protein of the invention.

By "vector" is meant a nucleic acid molecule, for example, a plasmid, cosmid, or bacteriophage, that is capable of replication in a host cell. In one embodiment, a vector is an expression vector that is a nucleic acid construct, generated recombinantly or synthetically, bearing a series of specified nucleic acid elements that enable transcription of a nucleic acid molecule in a host cell. Typically, expression is placed under the control of certain regulatory elements, including constitutive or inducible promoters, tissue-preferred regulatory elements, and enhancers.

BRIEF DESCRIPTION OF THE FIGURES

FIG. 2. Table showing downregulation of multiple miRs in the fibroblast-like LX2 following their co-culture with CCA cells. The table presents the Ct value and the qRT-PCR value normalized to U6. The ratio of qRT-PCR expression in LX2 cells cultured alone (control) or in the presence of cancer cells (F/CAFs) is highlighted in the right column.

Tumors were significantly smaller in animals that had been injected with miR-195-loaded EVs.

Figure 10:
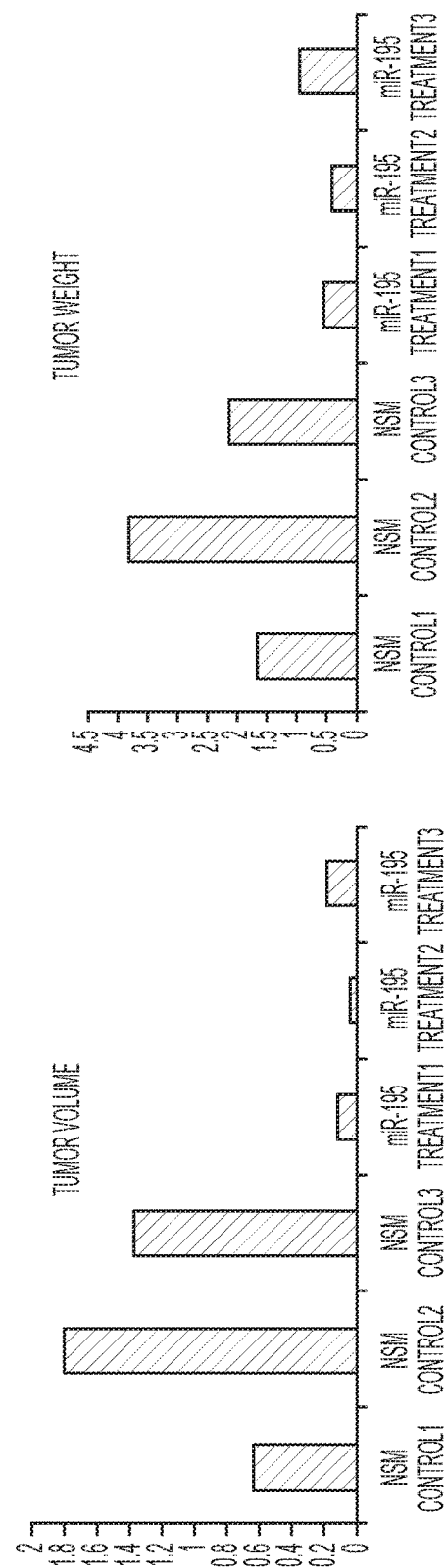

FIG. 10. miR-195-loaded EVs inhibit CCA tumor growth, as measured by volume (left graph), as well as weight (right graph). The tumors resected from rats were measured and weighed. The first 3 bars (front the left) in each graph represent 3 tumors from rats treated with the negative control (EVs-NSM), while the 3 bars on the right in each graph represent 3 tumors from rats treated with EVs-miR-195.

Figure 11:
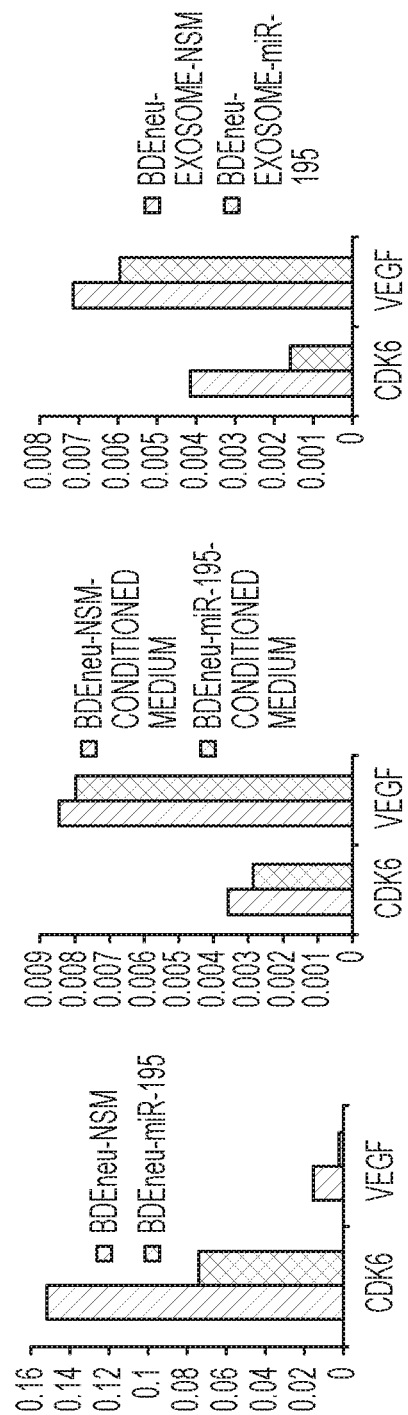

FIG. 11. miR-195 downregulates CDK6 and VEGF when directly transfected into BDEneu cells (left panel), when conditioned media from LX2 cells (treated with miR-195 or NSM) is utilized (middle panel), and when treated with exosomes loaded with miR-195 vs. NSM (right panel).

Figure 12:
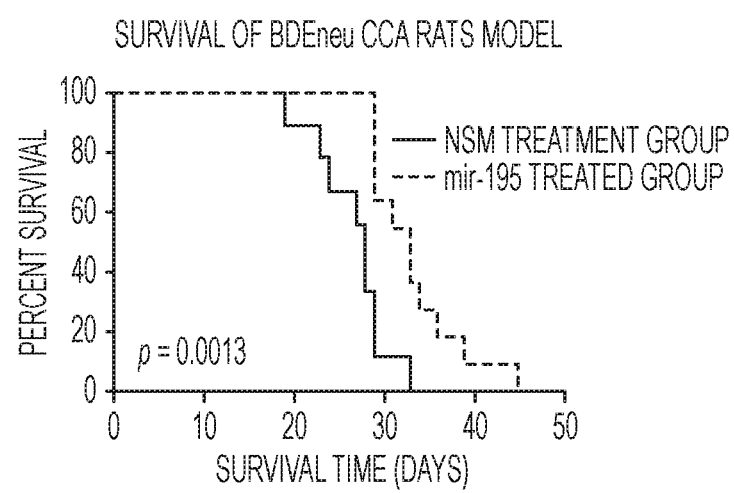

FIG. 12. Tail vein treatment of CCA with EVs-miR-195 increases the survival in rats by 50% vs. control.

Figure 13:
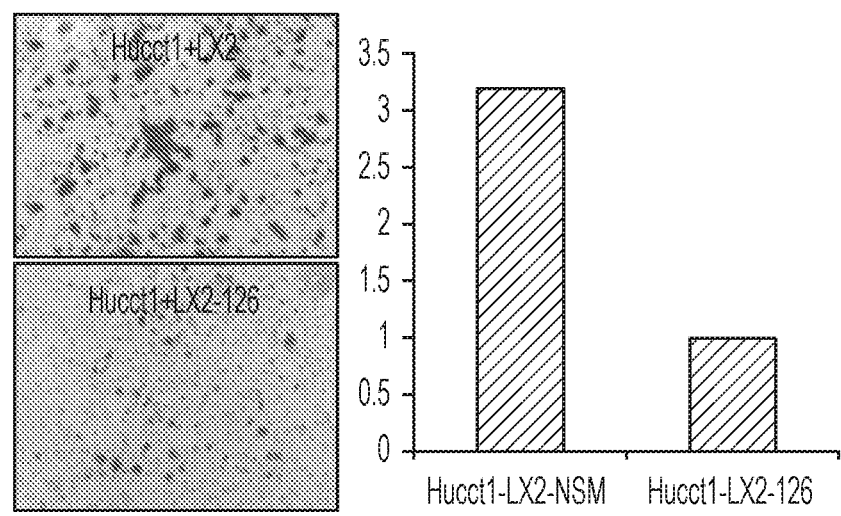

FIG. 13. LX2 cells expressing miR-126 inhibit CCA invasiveness in vitro. HuCCT1 cells were co-cultured directly with LX2 cells expressing either (upper image) a control miR, or (lower image) miR-126. Invasiveness of HuCCT1 cells was decreased 3.2 fold when co-cultured with LX2-126 cells.

Figure 14:
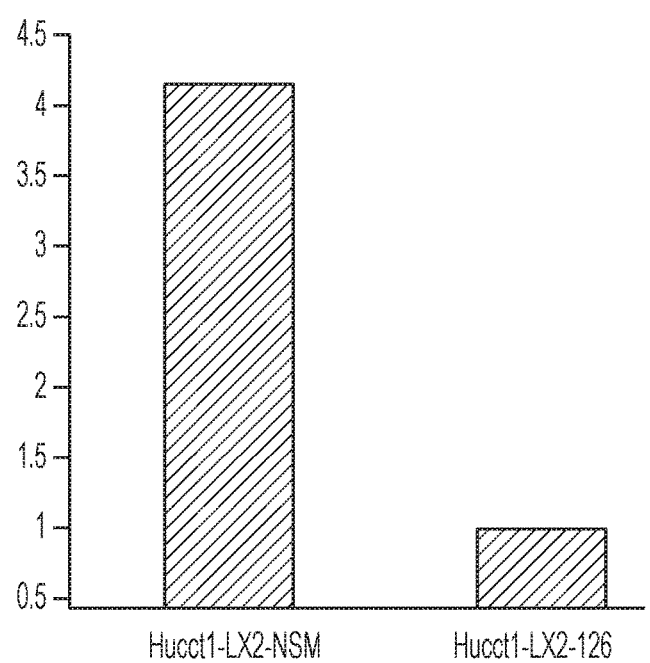
Figure 16A:
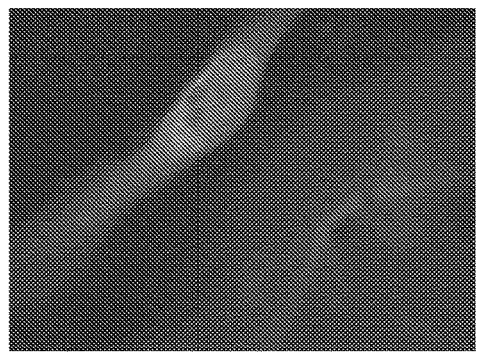
Figure 16B:
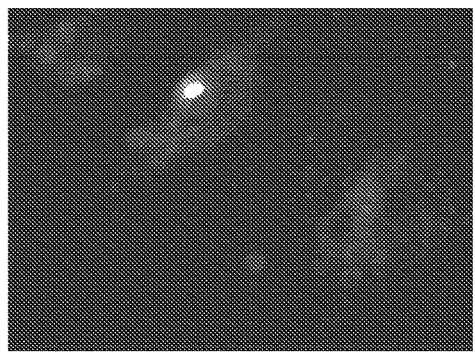
Figure 16C:
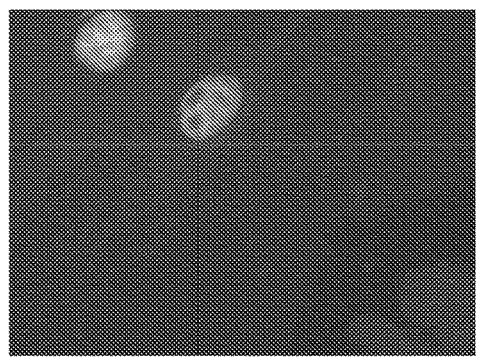
Figure 16D:
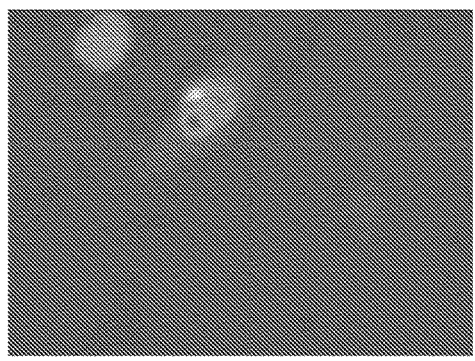

FIG. 14. LX2 cells expressing miR-126 inhibit CCA migration 4-fold in vitro. HuCCT1 cells were co-cultured directly with LX2 cells expressing either a controls miR or miR-126. Migration was measured in a scratch assay.

FIG. 15 Mammary fibroblast-derived EVs deliver a small molecule to breast cancer cells. MDA-MB-231 cells (stably expressing the fluorescent protein tdTomato) were grown in the presence of primary human mammary fibroblast cells that had previously been labeled with a fluorescent lipid (N-F-PE; N-fluorescein-phosphatidylethanolamine (Avanti polar lipids)) that is selectively secreted from human cells in EVs (Booth et al., J. Cell Biol. 2006; Fang et al., PLoS Biol. 2007). Over the course of 2-3 days, the (FIG. 15A) tdTomato-expressing human breast cancer (seen as white or light signal emitting cells on black and white drawings) cells took up the (FIG. 15B) EVs that had been released from the primary mammary fibroblast cell line. Cells were also stained with (FIG. 15C) DAPI to visualize the nucleus.

FIG. 16. Mammary fibroblast-derived EVs deliver a protein to breast cancer cells. MDA-MB-231 cells (stably expressing the fluorescent protein tdTomato) were grown in the presence of primary human mammary fibroblast cells that had previously been transfected with a plasmid designed to express Acyl-GFP, a form of GFP that is secreted from human cells in EVs. Over the course of 2-3 days, the (FIG. 16A) tdTomato-expressing human breast cancer cells took up the (FIG. 16B) the fluorescent lipid, N-F-PE labeled EVs that had been released from the primary mammary fibroblast cell line. Cells were also stained with (FIG. 16C) DAPI to visualize the nucleus, and (FIG. 16D) the images were merged to show the presence of CAF-derived EVs in the breast cancer cell (in this case, in the nucleus).

Figures 17A, 17B:
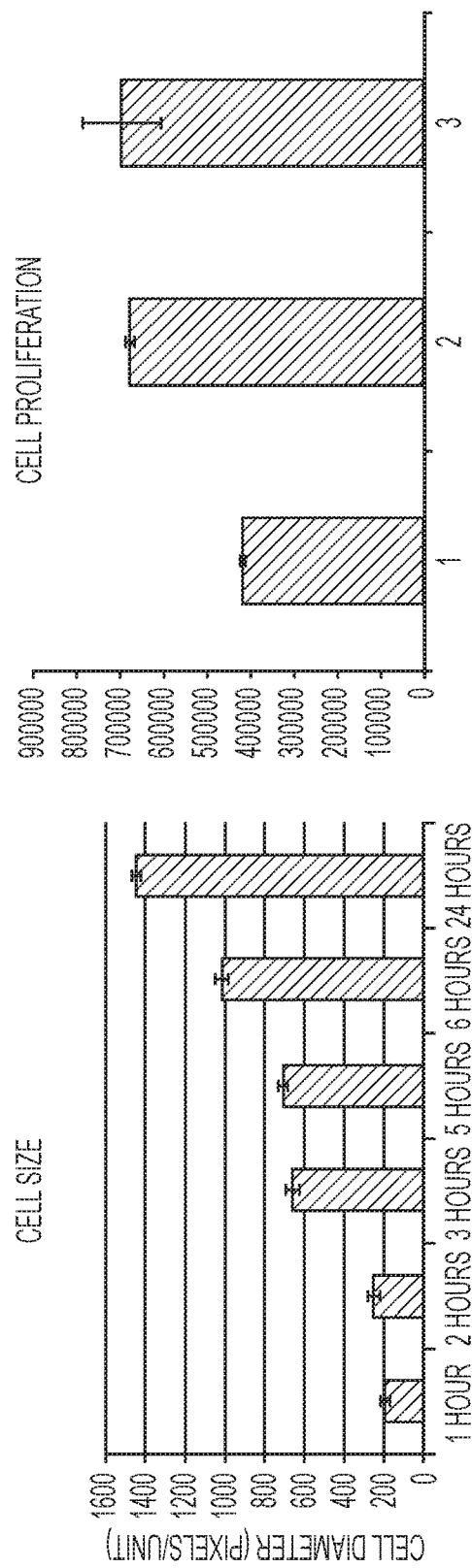

FIG. 17. Mammary fibroblasts promote the neoplastic phenotype of MDA-MB-231 breast cancer cells. MDA-MB-231 cells (stably expressing the red fluorescent protein tdTomato) were grown alone or in the presence of primary human mammary fibroblast cells. (A) The diameter of MDA-MB-231 cells grown on their own was approximately 200 relative units, but increased ~7-fold upon co-culture with CAFs, an increase in cell size that was apparent as early as 3 hours after co-culture with mammary fibroblasts and was complete within 1 day. Experiments were performed in triplicate, followed by calculation of average and standard deviation. Significant difference from t=1 hr (p,0.05) were observed for all but the 2 hr sample (B) Growth of MDA-MB-231 cells was induced ~2-fold by co-culture with mammary fibroblasts. MDA-MB-231 cells were plated on culture dishes. The next day, the disheswere either (1) grown on their own, or (2,3) were populated with mammary fibroblast (2) HMF line or (3) MMF line, to a density of ~20%. The next day the number of red MDA-MB-231 cells in each dish was counted. Experiments were performed in triplicate, and the averages and standard deviations showed significant differences between each experimental sample (p<0.05) from that of the control cancer cells grown on their own.

DETAILED DESCRIPTION OF THE INVENTION

The invention provides extracellular vesicles (EVs) derived from a cancer associated cell (e.g., fibroblast-like cell, stromal cell) comprising an agent (e.g., polypeptide, polynucleotide, small molecule), and methods of using such EVs to deliver the agent to a target cell.

The invention is based, at least in part, on the discovery that fibroblast gene expression is altered in fibroblasts that grow in proximity to cancer cells (e.g., in stroma) or in conditioned media where cancer cells had previously been cultured. Such cells are termed cancer associated fibroblasts (CAF). As reported in detail below, the gene expression of CAFs is altered following their growth in cancer conditioned media or in stroma. For example, CAFs have increased expression of CAF markers: alpha-smooth muscle actin (SMA), PDGFRbeta, and collagen. In one embodiment, a CAF expresses at least about 2-fold, 5-fold, 10-fold more alpha-SMA, PDGFRbeta, and collagen relative to a non-CAF fibroblast (i.e., a fibroblast derived from healthy non-cancerous tissue, or that has not been cultured in conditioned media derived from cancer cells). We show here that there is also a significant decrease in multiple miRs, including miR-195, miR-192 and miR-126. These microRNAs are involved in the transition from normal fibroblasts to CAFs. The overexpression of miR-195 in the CAF reverses many of the changes observed in not only in CAFs expressing mir-195, but in neighboring cells as well. Surprisingly, this effect was mediated by extracellular vesicles isolated from the mir-195 overexpressing cells. Levels of miR-195 were >60-fold higher in these EVs than in EVs isolated from control cells that were not over-expressing mir-195. In further experiments, cells over-expressing polypeptides and polynucleotides were found to shed EVs comprising increased levels of the over-expressed polypeptide or polynucleotide. When injected into rats having CCA, these fibroblast-derived vesicles were highly enriched within the CCA cells relative to non-cancer cells.

Accordingly, the invention provides extracellular vesicles (EVs) derived from CAFs that comprise an agent (e.g., polypeptide, polynucleotide, small molecule), and methods of using such EVs to selectively deliver the agent to a target cell (e.g., cancer cell) in vivo or in vitro.

Cholangiocarcinoma

Cholangiocarcinoma (CCA) is the second most common primary liver cancer. CCAs are very desmoplastic cancers (similar to pancreatic cancer, and some breast cancers). As described herein, we identified microRNA species that are relatively downregulated in fibroblast-like cells, along the continuum of inactive-to activated-to cancer associated-fibroblasts (CAFs). Studies in vitro showed that 'therapeutic' upregulation of these miR species in fibroblast-like cells resulted in less growth and invasiveness of neighboring cancer cells. Without intending to be bound by theory, it is likely that cancer-associated fibroblast-like cells play a regulatory role in CCA and other tumors. Thus, we have demonstrated that our therapy interferes with the signaling between fibroblast-like cells and cancer cells. The result is to restrict the growth and invasion of cancer. In understanding this signaling, as described herein, we demonstrated that transport of extracellular vesicles (EVs) between fibroblast like cells and cancer cells, in both the CCA model and in a breast cancer model, constitutes a rich signaling network which involves miRNAs and can also involve the transfer of proteins and lipids. We then engineered such EVs to contain as cargo the desired miR species, the desired protein, or the desired small molecule. The fibroblast cell-derived EVs are used to interfere with the signaling network that influences proliferation or invasion by cancer cells. Results described herein below indicate that EVs derived from fibroblast-like cells and loaded with microRNAs can affect the growth and invasion of cancer cells. Moreover, in vivo experiments demonstrated that EVs loaded with miRs can be systemically delivered and then selectively concentrate in liver tumors. This delivery was sufficient to decrease cancer growth and increase the overall survival (statistically significant) of treated animals. These fibroblast-like cell-derived EVs do not accumulate in normal liver cells, nor do these EVs accumulate in other tissues (e.g. kidney, lung, etc.).

In conclusion, our studies demonstrate the existence and functioning of EV exchange between fibroblast-like cells and cancer cells in two cancer models. We show that miRs loaded into EVs from fibroblast-like cells can have a functional role in control of the cancer cells. We show that EVs of fibroblast-like cell origin can be loaded with functional miRs, DNAs, proteins, and lipids. In addition, we show that EVs of fibroblast-like cell origin when loaded with miRs selectively target cancer cells in vivo and diminish their growth. Finally, EVs of fibroblast-like cell origin loaded with miRs can be systemically administered to animals bearing cancers with resulting reduction of tumor growth and resulting survival benefit.

Polynucleotides for Delivery

EVs derived EVs containing a microRNA may be used to deliver the microRNA to a target cell. MicroRNAs (miRNAs) are 20-24 nucleotide RNA molecules that regulate the stability or translational efficiency of target mRNAs. miRNAs have diverse functions including the regulation of cellular differentiation, proliferation, and apoptosis (Ambros, Nature 431, 350-5 (2004)). Although strict tissue- and developmental-stage-specific expression is critical for appropriate miRNA function, few mammalian transcription factors that regulate miRNAs have been identified.

In general, EVs of the invention comprise a polynucleotide that is downregulated in a cell of interest (e.g., cancer cell). The EV rescues the down regulation by increasing levels of the polynucleotide. In other embodiments, the EV provides a replacement polynucleotide that replaces or corrects a defective polynucleotide present in the cell.

In one embodiment, an EV derived from a fibroblast-like cell comprises a miR-195, miR-192, or miR-126 microRNA. In another embodiment, EV derived from a fibroblast-like cell comprises a nucleic acid sequence encoding a microRNA, such as miR from fibroblast-like cells can be used to deliver virtually any polynucleotide, including RNA, DNA, an antisense oligonucleotide, a short interfering RNA (siRNA), a short hairpin RNA (shRNA), or plasmid DNA polynucleotides and modified oligonucleotides. Exemplary siRNAs include siRNAs targeting Anti-RhoA/C, geranylgeranyl (or farnesyl) and transferase inhibitors of Ras activation, cerivastatin, palbococlib, also siRNA to CXCR4 in breast cancer metastases.

Polynucleotides provided in EVs include Mir-195, miR-192, or miR-126, as well as nucleic acid molecules.

In one embodiment, we have found that CCA cells alter the gene expression profile of surrounding fibroblasts, including reduced expression of miR-195; overexpression of miR-195 in CAFs is sufficient to inhibit CCA growth, migration, and invasion in vitro; miR-195 is secreted from CAFs within EVs; elevating miR-195 levels in CAFs is sufficient to up-regulate the levels of miR-195 in neighboring cancer cells; and intravenous injection of miR-195-loaded EVs inhibit CCA growth and extends survival in vivo.

Expression vectors having a polynucleotide with therapeutic function can be delivered to cells of a subject having a disease (e.g., cancer) using the EVs of the invention.

In a specific embodiment, the DNA encodes a protein with a specific function, either of diagnostic or therapeutic potential, such as Cre recombinase. In another embodiment, the nucleic acid molecule inhibits expression of a tumor suppressor gene as a way to induce a large animal model of cancer biology. In a more specific embodiment, the tumor suppressor gene is p53.

The EV comprising nucleic acid molecules are selectively delivered to target cells of a subject (e.g., cancer cells) in a form in which they are taken up and are advantageously expressed so that therapeutically effective levels can be achieved.

An isolated nucleic acid molecule can be manipulated using recombinant DNA techniques well known in the art. Thus, a nucleotide sequence contained in a vector in which 5' and 3' restriction sites are known, or for which polymerase chain reaction (PCR) primer sequences have been disclosed, is considered isolated, but a nucleic acid sequence existing in its native state in its natural host is not. An isolated nucleic acid may be substantially purified, but need not be. For example, a nucleic acid molecule that is isolated within a cloning or expression vector may comprise only a tiny percentage of the material in the cell in which it resides. Such a nucleic acid is isolated, however, as the term is used herein, because it can be manipulated using standard techniques known to those of ordinary skill in the art.

Transducing viral (e.g., retroviral, adenoviral, lentiviral and adeno-associated viral) vectors can be used for somatic cell gene therapy, especially because of their high efficiency of infection and stable integration and expression (see, e.g., Cayouette et al., Human Gene Therapy 8:423-430, 1997; Kido et al., Current Eye Research 15:833-844, 1996; Bloomer et al., Journal of Virology 71:6641-6649, 1997; Naldini et al., Science 272:263-267, 1996; and Miyoshi et al., Proc. Natl. Acad. Sci. U.S.A. 94:10319, 1997). For example, a polynucleotide can be cloned into a retroviral or other vector and expression can be driven from its endogenous promoter, from the retroviral long terminal repeat, or from a promoter specific for a target cell type of interest. Other viral vectors that can be used include, for example, a vaccinia virus, a bovine papilloma virus, or a herpes virus, such as Epstein-Barr Virus (also see, for example, the vectors of Miller, Human Gene Therapy 15-14, 1990; Friedman, Science 244:1275-1281, 1989; Eglitis et al., BioTechniques 6:608-614, 1988; Tolstoshev et al., Current Opinion in Biotechnology 1:55-61, 1990; Sharp, The Lancet 337: 1277-1278, 1991; Cornetta et al., Nucleic Acid Research and Molecular Biology 36:311-322, 1987; Anderson, Science 226:401-409, 1984; Moen, Blood Cells 17:407-416, 1991;

Miller et al., Biotechnology 7:980-990, 1989; Le Gal La Salle et al., Science 259:988-990, 1993; and Johnson, Chest 107:77S-83S, 1995). Retroviral vectors are particularly well developed and have been used in clinical settings (Rosenberg et al., N. Engl. J. Med 323:370, 1990; Anderson et al., U.S. Pat. No. 5,399,346).

Polynucleotide expression can be directed from any suitable promoter (e.g., the human cytomegalovirus (CMV), simian virus 40 (SV40), or metallothionein promoters), and regulated by any appropriate mammalian regulatory element. For example, if desired, enhancers known to preferentially direct gene expression in specific cell types can be used to direct the expression of a nucleic acid. The enhancers used can include, without limitation, those that are characterized as tissue- or cell-specific enhancers.

EVs derived from fibroblast-like cells can also be used to deliver nucleic acid molecules comprising a modified nucleic acid. Nucleic acid molecules include nucleobase oligomers containing modified backbones or non-natural internucleoside linkages. Oligomers having modified backbones include those that retain a phosphorus atom in the backbone and those that do not have a phosphorus atom in the backbone. For the purposes of this specification, modified oligonucleotides that do not have a phosphorus atom in their internucleoside backbone are also considered to be nucleobase oligomers. Nucleobase oligomers that have modified oligonucleotide backbones include, for example, phosphorothioates, chiral phosphorothioates, phosphorodithioates, phosphotriesters, aminoalkyl-phosphotriesters, methyl and other alkyl phosphonates including 3'-alkylene phosphonates and chiral phosphonates, phosphinates, phosphoramidates, thionophosphoramidates, thionoalkylphosphonates, thionoalkylphosphotriest-ers, and boranophosphates. Various salts, mixed salts and free acid forms are also included. Representative United States patents that teach the preparation of the above phosphorus-containing linkages include, but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; and 5,625,050, each of which is herein incorporated by reference.

Nucleobase oligomers having modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts. Representative United States patents that teach the preparation of the above oligonucleotides include, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439, each of which is herein incorporated by reference.

Nucleobase oligomers may also contain one or more substituted sugar moieties. Such modifications include 2'-O-methyl and 2'-methoxyethoxy modifications. Another desirable modification is 2'-dimethylaminooxyethoxy, 2'-aminopropoxy and 2'-fluoro. Similar modifications may also be made at other positions on an oligonucleotide or other nucleobase oligomer, particularly the 3' position of the sugar on the 3' terminal nucleotide. Nucleobase oligomers may also have sugar mimetics such as cyclobutyl moieties in place of the pentofuranosyl sugar. Representative United States patents that teach the preparation of such modified sugar structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; and 5,700,920, each of which is herein incorporated by reference in its entirety.

In other nucleobase oligomers, both the sugar and the internucleoside linkage, i.e., the backbone, are replaced with novel groups. Methods for making and using these nucleobase oligomers are described, for example, in "Peptide Nucleic Acids (PNA): Protocols and Applications" Ed. P. E. Nielsen, Horizon Press, Norfolk, United Kingdom, 1999. Representative United States patents that teach the preparation of PNAs include, but are not limited to, U.S. Pat. Nos. 5,539,082; 5,714,331; and 5,719,262, each of which is herein incorporated by reference. Further teaching of PNA compounds can be found in Nielsen et al., Science, 1991, 254, 1497-1500.

Polypeptide Delivery

The invention provides EVs comprising proteins. In a specific embodiment, the EV-delivered protein corrects a deficiency of the cell or subject, or induces the death of infected or deficient cells. Recombinant polypeptides of the invention are produced using virtually any method known to the skilled artisan. Typically, recombinant polypeptides are produced by transformation of a suitable host cell with all or part of a polypeptide-encoding nucleic acid molecule or fragment thereof in a suitable expression vehicle.

Those skilled in the field of molecular biology will understand that any of a wide variety of expression systems may be used to provide the recombinant protein. The precise host cell used is not critical to the invention. A polypeptide of the invention may be produced in a prokaryotic host (e.g., *E. coli*) or in a eukaryotic host (e.g., *Saccharomyces cerevisiae*, insect cells, e.g., Sf21 cells, or mammalian cells, e.g., NIH 3T3, HeLa, or preferably COS cells). Such cells are available from a wide range of sources (e.g., the American Type Culture Collection, Rockland, Md.; also, see, e.g., Ausubel et al., Current Protocol in Molecular Biology, New York: John Wiley and Sons, 1997). The method of transformation or transfection and the choice of expression vehicle will depend on the host system selected. Transformation and transfection methods are described, e.g., in Ausubel et al. (supra); expression vehicles may be chosen from those provided, e.g., in Cloning Vectors: A Laboratory Manual (P. H. Pouwels et al., 1985, Supp. 1987).

A variety of expression systems exist for the production of the polypeptides of the invention. EVs derived from fibroblast-like cells can be loaded with any one or more of the following expression vectors or with the polypeptides generated using such vectors. Expression vectors useful for producing polypeptides include, without limitation, chromosomal, episomal, and virus-derived vectors, e.g., vectors derived from bacterial plasmids, from bacteriophage, from transposons, from yeast episomes, from insertion elements, from yeast chromosomal elements, from viruses such as baculoviruses, papova viruses, such as SV40, vaccinia viruses, adenoviruses, fowl pox viruses, pseudorabies viruses and retroviruses, and vectors derived from combinations thereof.

One particular bacterial expression system for polypeptide production is the *E. coli* pET expression system (e.g., pET-28) (Novagen, Inc., Madison, Wis). According to this expression system, DNA encoding a polypeptide is inserted into a pET vector in an orientation designed to allow expression. Since the gene encoding such a polypeptide is under the control of the T7 regulatory signals, expression of the polypeptide is achieved by inducing the expression of T7 RNA polymerase in the host cell. This is typically achieved using host strains that express T7 RNA polymerase in response to IPTG induction. Once produced, recombinant polypeptide is then isolated according to standard methods known in the art, for example, those described herein.

Another bacterial expression system for polypeptide production is the pGEX expression system (Pharmacia). This system employs a GST gene fusion system that is designed for high-level expression of genes or gene fragments as fusion proteins with rapid purification and recovery of functional gene products. The protein of interest is fused to the carboxyl terminus of the glutathione S-transferase protein from *Schistosoma japonicum* and is readily purified from bacterial lysates by affinity chromatography using Glutathione Sepharose 4B. Proteins can be recovered under mild conditions by elution with glutathione. Cleavage of the glutathione S-transferase domain from the fusion protein is facilitated by the presence of recognition sites for site-specific proteases upstream of this domain. For example, proteins expressed in pGEX-2T plasmids may be cleaved with thrombin; those expressed in pGEX-3X may be cleaved with factor Xa.

Alternatively, recombinant polypeptides of the invention are expressed in *Pichia pastoris*, a methylotrophic yeast. *Pichia* is capable of metabolizing methanol as the sole carbon source. The first step in the metabolism of methanol is the oxidation of methanol to formaldehyde by the enzyme, alcohol oxidase. Expression of this enzyme, which is coded for by the AOX1 gene is induced by methanol. The AOX1 promoter can be used for inducible polypeptide expression or the GAP promoter for constitutive expression of a gene of interest.

Once the recombinant polypeptide of the invention is expressed, it is isolated, for example, using affinity chromatography. In one example, an antibody (e.g., produced as described herein) raised against a polypeptide may be attached to a column and used to isolate the recombinant polypeptide. Lysis and fractionation of polypeptide-harboring cells prior to affinity chromatography may be performed by standard methods (see, e.g., Ausubel et al., supra). Alternatively, the polypeptide is isolated using a sequence tag, such as a hexahistidine tag (SEQ ID NO: 4), that binds to nickel column.

Once isolated, the recombinant protein can, if desired, be further purified, e.g., by high performance liquid chromatography (see, e.g., Fisher, Laboratory Techniques In Biochemistry and Molecular Biology, eds., Work and Burdon, Elsevier, 1980). Polypeptides of the invention, particularly short peptide fragments, can also be produced by chemical synthesis (e.g., by the methods described in Solid Phase Peptide Synthesis, 2nd ed., 1984 The Pierce Chemical Co., Rockford, Ill.). These general techniques of polypeptide expression and purification can also be used to produce and isolate useful peptide fragments or analogs (described herein).

The isolated polypeptides or fragments are loaded into EVs as described herein.

Antibody Delivery

Like other polypeptides, antibodies can be delivered using EVs derived from fibroblast-like cells or CAFs. Antibodies can be made by any of the methods known in the art utilizing a polypeptide interest, or immunogenic fragments thereof, as an immunogen. One method of obtaining antibodies is to immunize suitable host animals with an immunogen and to follow standard procedures for polyclonal or monoclonal antibody production. The immunogen will facilitate presentation of the immunogen on the cell surface Immunization of a suitable host can be carried out in a number of ways. Nucleic acid sequences encoding a polypeptide of the invention or immunogenic fragments thereof, can be provided to the host in a delivery vehicle that is taken up by immune cells of the host. The cells will in turn express the receptor on the cell surface generating an immunogenic response in the host. Alternatively, nucleic acid sequences encoding the polypeptide, or immunogenic fragments thereof, can be expressed in cells in vitro, followed by isolation of the polypeptide and administration of the polypeptide to a suitable host in which antibodies are raised.

Alternatively, antibodies against the polypeptide may, if desired, be derived from an antibody phage display library. A bacteriophage is capable of infecting and reproducing within bacteria, which can be engineered, when combined with human antibody genes, to display human antibody proteins. Phage display is the process by which the phage is made to 'display' the human antibody proteins on its surface. Genes from the human antibody gene libraries are inserted into a population of phage. Each phage carries the genes for a different antibody and thus displays a different antibody on its surface.

Antibodies made by any method known in the art can then be purified from the host. Antibody purification methods may include salt precipitation (for example, with ammonium sulfate), ion exchange chromatography (for example, on a cationic or anionic exchange column run at neutral pH and eluted with step gradients of increasing ionic strength), gel filtration chromatography (including gel filtration HPLC), and chromatography on affinity resins such as protein A, protein G, hydroxyapatite, and anti-immunoglobulin.

Antibodies can be conveniently produced from hybridoma cells engineered to express the antibody. Methods of making hybridomas are well known in the art. The hybridoma cells can be cultured in a suitable medium, and spent medium can be used as an antibody source. Polynucleotides encoding the antibody of interest can in turn be obtained from the hybridoma that produces the antibody, and then the antibody may be produced synthetically or recombinantly from these DNA sequences. For the production of large amounts of antibody, it is generally more convenient to obtain an ascites fluid. The method of raising ascites generally comprises injecting hybridoma cells into an immunologically naive histocompatible or immunotolerant mammal, especially a mouse. The mammal may be primed for ascites production by prior administration of a suitable composition (e.g., Pristane).

In particular embodiments, the EV comprises an antibody against a tumor antigen (e.g., an antigen associated with breast cancer tumor, pancreatic tumor, glioblastoma, melanoma, lung cancer tumor, ovarian cancer tumor). In another embodiment, the antibody comprises an antibody that targets a protein expressed in the blood vessels supplying the tumor. In yet another embodiment, the antibody targets a protein that functions in miRNA maturation, checkpoint blocking, or that is histone specific.

Small Molecule Delivery

EVs derived from fibroblast-like cells are used to deliver therapeutic or imaging agents. In one embodiment, the invention provides an EV comprising, for example, N-fluorescein phosphatidylethanolamine (N-F-PE), doxorubicin, or cisplatin. In other embodiments, an EV described herein a conventional chemotherapeutic agent including, but not limited to, alemtuzumab, altretamine, aminoglutethimide, amsacrine, anastrozole, azacitidine, bleomycin, bicalutamide, busulfan, capecitabine, carboplatin, carmustine, celecoxib, chlorambucil, 2-chlorodeoxyadenosine, cisplatin, colchicine, cyclophosphamide, cytarabine, cytoxan, dacarbazine, dactinomycin, daunorubicin, docetaxel, doxorubicin, epirubicin, estramustine phosphate, etodolac, etoposide, exemestane, floxuridine, fludarabine, 5-fluorouracil, flutamide, formestane, gemcitabine, gentuzumab, goserelin, hexamethylmelamine, hydroxyurea, hypericin, ifosfamide, imatinib, interferon, irinotecan, letrozole, leuporelin, lomustine, mechlorethamine, melphalen, mercaptopurine, 6-mercaptopurine, methotrexate, mitomycin, mitotane, mitoxantrone, nilutamide, nocodazole, paclitaxel, pentostatin, procarbazine, raltitrexed, rituximab, rofecoxib, streptozocin, tamoxifen, temozolomide, teniposide, 6-thioguanine, topotecan, toremofine, trastuzumab, vinblastine, vincristine, vindesine, and vinorelbine.

In particular embodiments, the EV comprises sirolimus, evirolimus, lapatinib, or olaparib.

Delivery of Imaging Agents

EVs comprising a detectable agent are useful for imaging studies. The invention provides an EV comprising any one of the following exemplary small molecules useful in imaging: carbocyanine, indocarbocyanine, oxacarbocyanine, thüicarbocyanine and merocyanine, polymethine, coumarine, rhodamine, xanthene, fluorescein, borondipyrromethane (BODIPY), Cy5, Cy5.5, Cy7, VivoTag-680, VivoTag-S680, VivoTag-S750, AlexaFluor660, AlexaFluor680, AlexaFluor700, AlexaFluor750, AlexaFluor790, Dy677, Dy676, Dy682, Dy752, Dy780, DyLight547, Dylight647, HiLyte Fluor 647, HiLyte Fluor 680, HiLyte Fluor 750, IRDye 800CW, IRDye 800RS, IRDye 700DX, ADS780WS, ADS830WS, and ADS832WS.

In other embodiments, the EV comprises a nanoparticle useful in imaging studies. In one embodiment, nanoparticles are synthesized using a biodegradable shell known in the art. In one embodiment, a polymer, such as poly (lactic-acid) (PLA) or poly (lactic-co-glycolic acid) (PLGA) is used. Such polymers are biocompatible and biodegradable, and are subject to modifications that desirably increase the circulation lifetime of the nanoparticle. In one embodiment, nanoparticles are modified with polyethylene glycol (PEG), which increases the half-life and stability of the particles in circulation (Gref et al., Science 263(5153): 1600-1603, 1994).

Biocompatible polymers useful in the composition and methods of the invention include, but are not limited to, polyamides, polycarbonates, polyalkylenes, polyalkylene glycols, polyalkylene oxides, polyalkylene terephthalates, polyvinyl alcohols, polyvinyl ethers, polyvinyl esters, polyvinyl halides, polyvinylpyrrolidone, polyglycolides, polysiloxanes, polyurethanes and copolymers thereof, alkyl cellulose, hydroxyalkyl celluloses, cellulose ethers, cellulose esters, nitro celluloses, polymers of acrylic and methacrylic esters, methyl cellulose, ethyl cellulose, hydroxypropyl cellulose, hydroxypropyl methyl cellulose, hydroxybutyl methyl cellulose, cellulose acetate, cellulose propionate, cellulose acetate butyrate, cellulose acetage phthalate, carboxylethyl cellulose, cellulose triacetate, cellulose sulphate sodium salt, poly(methyl methacrylate), poly(ethylmethacrylate), poly(butylmethacrylate), poly(isobutylmethacryla-te), poly(hexlmethacrylate), poly(isodecylmethacrylate), poly(lauryl methacrylate), poly(phenyl methacrylate), poly(methyl acrylate), poly(isopropyl acrylate), poly(isobutyl acrylate), poly(octadecyl acrylate), polyethylene, polypropylene poly(ethylene glycol), poly(ethylene oxide), poly (ethylene terephthalate), poly(vinyl alcohols), poly(vinyl acetate, poly vinyl chloride polystyrene, polyvinylpryrrolidone, polyhyaluronic acids, casein, gelatin, glutin, polyanhydrides, polyacrylic acid, alginate, chitosan, poly(methyl methacrylates), poly(ethyl methacrylates), poly(butylmethacrylate), poly(isobutylmethacrylate), poly (hexlmethacrylate), poly(isodecl methacrylate), poly(lauryl methacrylate), poly(phenyl methacrylate), poly(methyl acrylate), poly(isopropyl acrylate), poly(isobutyl acrylate), poly(octadecl acrylate) and combinations of any of these. In one embodiment, the nanoparticles of the invention include PEG-PLGA polymers.

In response to the growing need for encapsulation materials, several different routes to producing hollow polymeric capsules are available. In one example, the shell is composed of dendrimers (Zhao, M., et al. J. Am. Chem. Soc. (1998) 120:4877). A dendrimer is an artificially manufactured or synthesized large molecule comprised of many smaller ones linked together—built up from branched units called monomers. Technically, dendrimers are a unique class of a polymer, about the size of an average protein, with a compact, tree-like molecular structure, which provides a high degree of surface functionality and versatility. Their shape gives them vast amounts of surface area, making them useful building blocks and carrier molecules at the nanoscale and they come in a variety of forms, with different physical (including optical, electrical and chemical) properties. In other embodiments, the shell comprises block copolymers (Thurmond, K. B., II, et al. J. Am. Chem. Soc. (1997) 119:6656; Macknight, W. J., et al., Acc. Chem. Res. (1998) 31:781; Harada, A. and Kataoka, K. Science (1999), 283: 65), vesicles (Hotz, J. and Meier, W. Langmuir (1998) 14:1031; Discher, B. M., et al., Science (1999) 284:1143), hydrogels (Kataoka, K. et al. J. Am. Chem. Soc. (1998) 120:12694) and template-synthesized microtubules (Martin, C. R. and Parthasarathy, R. V. Adv. Mater. (1995) 7:487) that are capable of encapsuling a photosensitizer.

In another embodiment, EV of the invention comprises an isotopic label for positron or scintillation or SPECT imaging.

In another embodiment, an EV of the invention comprises a magnetic nanoparticle that has a high magnetic moment to enhance the selectivity of the nanoparticle for detection. In another embodiment, a magnetic nanoparticle includes a magnetic core and a biocompatible outer shell, in which the outer shell both protects the core from oxidation and enhances magnetic properties of the nanoparticle. The enhanced magnetic properties can include increased magnetization and reduced coercivity of the magnetic core, allowing for highly sensitive detection as well as diminished non-specific aggregation of nanoparticles. By forming biocompatible nanoparticles having enhanced magnetic properties, detection of specific target proteins and cells is provided. In one embodiment, a nanoparticle core is formed from ferromagnetic materials that are crystalline, polycrystalline, or amorphous in structure. For example, the nanoparticle core can include materials such as, but not limited to, Fe, Co, Ni, $FeOFe_2O_3$, $NiOFe_2O_3$, $CuOFe_2O_3$, $MgOFe_2O_3$, MnBi, MnSb, $MnOFe_2O_3$, $Y3Fe_5Oi_2$, $CrO_2$, MnAs, SmCo, FePt, or combinations thereof.

In another embodiment, the outer shell of the magnetic nanoparticle partially or entirely surrounds the nanoparticle core. In some implementations, the shell is formed from a superparamagnetic material that is crystalline, poly-crystalline, or amorphous in structure. In some cases, the material used to form the shell is biocompatible, i.e., the shell material elicits little or no adverse biological/immune response in a given organism and/or is nontoxic to cells and organs. Exemplary materials that can be used for the shell include, but are not limited to, metal oxides, e.g., ferrite ($Fe_3C"4$), FeO, Fe203, $CoFe_2O4$, $MnFe_2O4$, $NiFe_2O4$, $ZnMnFe_2O4$, or combinations thereof.

Methods of making and delivering nanoparticles are known in the art and described, for example, in the following US Patent Publications: 20150258222, 20140303022, 20130309170, and 20130195767.

Extracellular Vesicle Isolation, Loading, and Targeting

EVs defined herein are generated as described herein below. In general, the EVs are released by cells (e.g., CAFs, fibroblast-like cells) into the extracellular environment. In vivo, EVs are isolated from a variety of biological fluids, including but not limited to, blood, plasma, serum, urine, stool, semen, cerebrospinal fluid, prostate fluid, lymphatic drainage, bile fluid, and pancreatic secretions. The EVs are then separated using routine methods known in the art. In one embodiment, EVs are isolated from the supernatants of cultured cells using differential ultracentrifugation. In another embodiment, EVs are separated from nonmembranous particles, using their relatively low buoyant density (Raposo et al., 1996; Escola et al., 1998; van Niel et al., 2003; Wubbolts et al., 2003). Kits for such isolation are commercially available, for example, from Qiagen, InVitrogen and SBI.

Methods for loading EVs with agent are known in the art and include lipofection, electroporation, as well as any standard transfection method.

In one embodiment, the EVs comprising a polynucleotide or polypeptide or small molecule of interest are obtained by over-expressing the polynucleotide or polypeptide or loading the cells with the small molecule in culture and subsequently isolating indirectly modified EVs from the cultured cells. In another embodiment, EVs comprising a polynucleotide or polypeptide or small molecule of interest are generated by loading previously purified EVs with the molecule(s) of interest into/onto the EVs by electroporation (polynucleotide or polypeptide), covalent or non-covalent coupling to the EV surface (polynucleotide or polypeptide or small molecule) or simple co-incubation (polynucleotide or polypeptide or small molecule).

In general, the physical properties of EVs of the invention are sufficient to target the EV to a cancer cell of interest (e.g., breast cancer tumor, pancreatic tumor, glioblastoma, melanoma, lung cancer tumor, ovarian cancer tumor). Nevertheless, in particular embodiments, it may be useful to derivatize the EV with an antibody that selectively binds to a tumor antigen. Targeted EVs may be loaded with an agent that is particularly effective against the targeted cancer cell. Exemplary target factors and agents are provided in Table 1 (below).

| Target factor | Expression cell | Function | Drug | Mechanism | Clinical Trial |
|---|---|---|---|---|---|
| VEGF | tumor cells CAFs, TAMs. | Angiogenesis | Bevacizumab | Neutralization VEGF | Phase II |
|  |  |  | Adsfit | Interception of VEGF | Preclinical |
|  |  |  | IMC-1C11 | anit-VEGFR-2 antibody | Phase I |
|  |  |  | RPI.4610 | anti-VEGFR-1 ribozyme | Phase II |
| Tenascin-C | CAFs, cancer cells | cell adhesion | 81C6 | radioimmunotherapy | Phase II |
|  |  |  | ATN-RNA | siRNA | Phase I |
| FAP | CAFs, TECs, cancer cells | Serine protease | PT-100 | activity inhibitor | Phase I |
|  |  |  | Sibrotuzumab | anti-FAP antibody | Phase I |
|  |  |  | Sc40-FasL | induce apoptosis of FAP+ cells | preclinical |
|  |  |  | Rebimastat | activity inhibitor | Phase III |
| CTGF | CAFs, TECs, cancer cell, neural | Growth factor | FG-3019 | anti-CTGF antibody | preclinical |
|  |  |  | DN-9693 | degrade mRNA | preclinical |
| MMPs | CAFs, TECs, TAMs, cancer cells | metalloproteinases | Marimastat | activity inhibitor | Phase III |
|  |  |  | Tanomastat | activity inhibitor | Phase III |
|  |  |  | Rebimastat | activity inhibitor | Phase III |
| uPA | CAFs, TAMs, cancer cells | Serine protease | PAI-2 | activity inhibitor | preclinical |
|  |  |  | uPA-UT1 | activIty inhibitor | preclinical |
| CA IX | CAFs, cancer cells | Carbonic anhydrase | Rencarex WX-G250 | induce ADCC | Phase III |

Pharmaceutical Compositions

The invention provides EVs for the delivery of therapeutic compositions that specifically deliver an agent (e.g., polynucleotide, polypeptide, or small molecule for the treatment of disease. In one embodiment, the present invention provides a pharmaceutical composition comprising an EV derived from a CAF or stromal cell. EVs of the invention may be administered as part of a pharmaceutical composition. In general, EVs are provided in a physiologically balanced saline solution. The solution comprising the EVs is stored at room temperature for up to about 24 hours, for longer than twenty four hours such solutions can be stored at about four degrees Celsius for days, weeks, or months. EVs are frozen for long term storage up to 10 years. The compositions should be sterile and contain a therapeutically effective amount of the EV in a unit of weight or volume suitable for administration to a subject.

EVs of the invention may be administered within a pharmaceutically-acceptable diluent, carrier, or excipient, in unit dosage form. Conventional pharmaceutical practice may be employed to provide suitable formulations or compositions to administer the compounds to patients suffering from a disease (e.g., cancer). Administration may begin before the patient is symptomatic. Any appropriate route of administration may be employed, for example, administration may be parenteral, intravenous, intraarterial, subcutaneous, intratumoral, intramuscular, intracranial, intraorbital, ophthalmic, intraventricular, intrahepatic, intracapsular, intrathecal, intracisternal, intraperitoneal, intranasal, aerosol, suppository, or oral administration. For example, therapeutic formulations may be in the form of liquid solutions or suspensions; for oral administration, formulations may be in the form of tablets or capsules; and for intranasal formulations, in the form of powders, nasal drops, or aerosols.

Methods well known in the art for making formulations are found, for example, in "Remington: The Science and Practice of Pharmacy" Ed. A. R. Gennaro, Lippincourt Williams & Wilkins, Philadelphia, Pa., 2000. Formulations for parenteral administration may, for example, contain excipients, sterile water, or saline, polyalkylene glycols such as polyethylene glycol, oils of vegetable origin, or hydrogenated napthalenes. Biocompatible, biodegradable lactide polymer, lactide/glycolide copolymer, or polyoxyethylene-polyoxypropylene copolymers may be used to control the release of the compounds. Other potentially useful parenteral delivery systems for microRNA molecules include ethylene-vinyl acetate copolymer particles, osmotic pumps, implantable infusion systems, and liposomes. Formulations for inhalation may contain excipients, for example, lactose, or may be aqueous solutions containing, for example, polyoxyethylene-9-lauryl ether, glycocholate and deoxycholate, or may be oily solutions for administration in the form of nasal drops, or as a gel.

The formulations can be administered to human patients in therapeutically effective amounts (e.g., amounts which prevent, eliminate, or reduce a pathological condition) to provide therapy for a disease or condition. The preferred dosage of an EV of the invention is likely to depend on such variables as the type and extent of the disorder, the overall health status of the particular patient, the formulation of the compound excipients, and its route of administration.

With respect to a subject having a neoplastic disease or disorder, an effective amount is sufficient to stabilize, slow, or reduce the proliferation of the neoplasm. Generally, doses of active polynucleotide compositions of the present invention would be from about 0.01 mg/kg per day to about 1000 mg/kg per day. It is expected that doses ranging from about 50 to about 2000 mg/kg will be suitable. Lower doses will result from certain forms of administration, such as intravenous administration. In the event that a response in a subject is insufficient at the initial doses applied, higher doses (or effectively higher doses by a different, more localized delivery route) may be employed to the extent that patient tolerance permits. Multiple doses per day are contemplated to achieve appropriate systemic levels of EVs A variety of administration routes are available. The methods of the invention, generally speaking, may be practiced using any mode of administration that is medically acceptable, meaning any mode that produces effective levels of the active compounds without causing clinically unacceptable adverse effects. Other modes of administration include oral, rectal, topical, intraocular, buccal, intravaginal, intracisternal, intracerebroventricular, intratracheal, nasal, transdermal, within/on implants, e.g., fibers such as collagen, osmotic pumps, or grafts comprising appropriately transformed cells, etc., or parenteral routes.

Therapy

Results provided herein below show that conditioned media from cancer cells can be used to alter a fibroblast-like cell's gene expression and physiology to promote cancer growth. These cancer-promoting changes in fibroblast-like cells include changes in the exosomes/EVs (and other signals) that they deliver to neighboring cancer cells. The invention provides methods for using a fibroblast-like cell-derived EVs to reverse these changes and inhibit cancer cell growth in vitro and in vivo. In one embodiment of the present invention, fibroblast-like cell-derived exosomes/EVs can be engineered to deliver anti-neoplastic, therapeutic miRs in vivo. In this embodiment, the fibroblast-like cells represent both localized cells of endothelial origin, localized tissue pleuripotential stem cells which develop fibroblast phenotypes or endogenous stem cells of bone marrow origin which have migrated to the site of tumor.

Yet another embodiment of the present invention is a cancer therapy that interrupts the support that stroma provides to cancer cells, in the context of CCA, in the context of breast cancer, and more broadly with potential to all cancers. Although there are therapeutic strategies to kill cancer cells (from conventional chemotherapy to targeted molecular therapies), there are currently no FDA-approved therapies to interrupt the support that stroma provides to cancer cells. Another embodiment of the present invention utilizes EV-mediated miR transfer from stromal cells to cancer cells to create a therapeutic with anti-neoplastic and survival-extending properties in vivo.

Other embodiments of the present invention target other cancers, including breast cancer, as well as cancers with pronounced fibrosis. Some of the most aggressive cancers, such as pancreatic, breast, and hepatocellular carcinoma, develop a close symbiotic relationship with fibroblast-like cells, and we have shown that this relationship has strong supporting effects on both CCA and breast cancer cells Therapy may be provided wherever cancer or other disease therapy is performed: at home, the doctor's office, a clinic, a hospital's outpatient department, or a hospital. Treatment generally begins at a hospital so that the doctor can observe the therapy's effects closely and make any adjustments that are needed. The duration of the therapy depends on the kind of cancer being treated, the age and condition of the patient, the stage and type of the patient's disease, and how the patient's body responds to the treatment. Drug administration may be performed at different intervals (e.g., daily, weekly, or monthly). Therapy may be given in on-and-off cycles that include rest periods so that the patient's body has a chance to build healthy new cells and regain its strength.

Depending on the type of disease and its stage of development, the therapy can be used to slow the spreading of the cancer, to slow the cancer's growth, to kill or arrest cancer cells that may have spread to other parts of the body from the original tumor, to relieve symptoms caused by the cancer, or to prevent cancer in the first place. As described above, if desired, treatment with an agent of the invention may be combined with conventional therapies, including therapies for the treatment of proliferative disease (e.g., radiotherapy, surgery, or chemotherapy). For any of the methods of application described above, an EV of the invention is desirably administered intravenously or is applied to the site of neoplasia (e.g., by injection).

In particular embodiments, EVs can be used to deliver therapeutic miRs in vivo, without obvious involvement of normal liver cells nor development of a cellular inflammatory reaction. Furthermore, the specific finding is that CAF derived EV-based therapy utilizing miRs delivered by EVs in particular embodiments herein targets the cancer-stroma niche interactions, an important property of cancers that is not currently addressed by prior art nor any FDA-approved agents. EVs contribute to CAF-mediated support of CCA, and that miR-loaded, fibroblast-derived EVs can slow the growth of CCA and prolong survival in vivo. One embodiment of the present invention is a therapeutic with anti-proliferation, anti-spread and with survival-extending properties in vivo.

Kits

Kits of the invention include EVs comprising an agent formulated for delivery to a cell in vitro or in vivo. Optionally, the kit includes directions for delivering the EV to a subject. In other embodiments, the kit comprises a sterile container which contains the EV; such containers can be boxes, ampules, bottles, vials, tubes, bags, pouches, blister-packs, or other suitable container form known in the art. Such containers can be made of plastic, glass, laminated paper, metal foil, or other materials suitable for holding nucleic acids. The instructions will generally include information about the use of the EV. In other embodiments, the instructions include at least one of the following: description of the EV; methods for using the enclosed materials for the treatment of a disease, including a cancer; precautions; warnings; indications; clinical or research studies; and/or references. The instructions may be printed directly on the container (when present), or as a label applied to the container, or as a separate sheet, pamphlet, card, or folder supplied in or with the container.

Transgenic Animals

In another aspect, the EVs of the present invention can be used to create animal models (including large animals such as swine, canine, primate and the like) of particular diseases including, but not limited to, cancer. For example, the EVs can be manipulated to contain genetic material comprising a transposon system (e.g., sleeping beauty) encoding an oncogene. In another embodiment, genetic material comprises a plasmid encoding an oncogene. In a further embodiment, the genetic material comprises a viral vector encoding an oncogene. The oncogene can include, but is not limited to, one or more of c-Myc, K-Ras, N-Ras, c-Met, AKT, P53, P16, CTNNB1, AXIN1, AXIN2, TP53, PIK3CA, PTEN, MET.

Another embodiment of the present invention utilizes one or more of the therapies described in the present patent application in conjunction with one or more cancer therapies, such as surgery, chemotherapy, radiation, and targeted molecular therapies.

Without further elaboration, it is believed that one skilled in the art, using the preceding description, can utilize the present invention to the fullest extent. The following examples are illustrative only, and not limiting of the remainder of the disclosure in any way whatsoever.

EXAMPLES

The following examples are put forth so as to provide those of ordinary skill in the art with a complete disclosure and description of how the compounds, compositions, articles, devices, and/or methods described and claimed herein are made and evaluated, and are intended to be purely illustrative and are not intended to limit the scope of what the inventors regard as their invention. Efforts have been made to ensure accuracy with respect to numbers (e.g., amounts, temperature, etc.) but some errors and deviations should be accounted for herein. Unless indicated otherwise, parts are parts by weight, temperature is in degrees Celsius or is at ambient temperature, and pressure is at or near atmospheric. There are numerous variations and combinations of reaction conditions, e.g., component concentrations, desired solvents, solvent mixtures, temperatures, pressures and other reaction ranges and conditions that can be used to optimize the product purity and yield obtained from the described process. Only reasonable and routine experimentation will be required to optimize such process conditions.

Cholangiocarcinoma (CCA), pancreatic cancer, and other cancers induce a strong desmoplastic reaction that includes intimate contact between cancer cells and tissue fibroblasts.

The vast majority of hepatocellular cancers (HCC) arise in a fibrotic liver. This fibrotic response was long assumed to have antineoplastic effects, but recent studies support a new paradigm in which cancer-associated fibroblasts (CAFs) play a supporting role in cancer growth and metastasis (Mueller M M, Fusenig N E. Friends or foes—bipolar effects of the tumor stroma in cancer. Nat Rev Cancer 2004; 4:839-49). For example, removing CAFs inhibits CCA growth, while CAF-derived PDGF, Periostin, Tenascin-C, Thrombospondin-I, and Galectin-1 are known to promote tumor growth (Sirica A E, Dumur C I, Campbell D J, et al. Intrahepatic cholangiocarcinoma progression: prognostic factors and basic mechanisms. Clin Gastroenterol Hepatol 2009; 7:568-78; Kawahara N, Ono M, Taguchi K, et al. Enhanced expression of thrombospondin-1 and hypovascularity in human cholangiocarcinoma. Hepatology 1998; 28:1512-7; Shimonishi T, Miyazaki K, Kono N, et al. Expression of endogenous galectin-1 and galectin-3 in intrahepatic cholangiocarcinoma. Hum Pathol 2001; 32:302-10). These observations fit within a broader paradigm in which cancer cells prime stroma to support cancer growth and metastasis (Wan L, Pantel K, Kang Y. Tumor metastasis: moving new biological insights into the clinic. Nat Med 2013; 19:1450-64; Hood J L, San R S, Wickline S A. Exosomes released by melanoma cells prepare sentinel lymph nodes for tumor metastasis. Cancer Res 2011; 71:3792-801) in a bidirectional interplay of signaling reactions (Roccaro A M, Sacco A, Maiso P, et al. BM mesenchymal stromal cell-derived exosomes facilitate multiple myeloma progression. J Clin Invest 2013; 123:1542-55).

Figure 1:
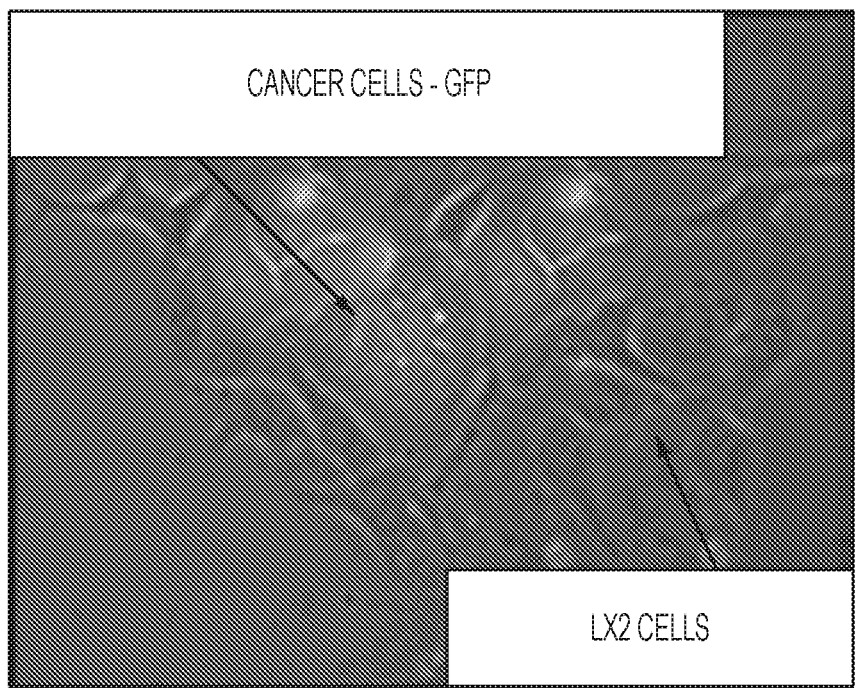
FIG. 1. An image of a co-culture of cancer cells and the fibroblast-like (e.g. fibroblasts, stellate cells, etc.) cell, LX-2 (. HuCCT1 CCA cells are marked with EGFP and LX2 fibroblasts are unstained.

Example 1: Co-culturing Fibroblasts and Cancer Cells Leads to Down-Regulation of Specific miRs within Fibroblasts The hypothesis that cancer cells derive support from their stroma is based on a number of observations, one of which is the fact that cancer cells alter the physiology and gene expression patterns of their surrounding cells. In the case of CCA and other gastrointestinal tumors, tissue fibroblasts and their extracellular matrix (ECM) are major components of the tumor stroma. To determine if CCA cancer cells affect fibroblast gene expression patterns, we generated fluorescent CCA cell lines by infecting them with MSCV-IRES-EGFP (MIEG3), a retrovirus that expresses enhanced-GFP (EGFP) (Olaru A V, Ghiaur G, Yamanaka S, et al. A microRNA downregulated in human cholangiocarcinoma controls cell cycle through multiple targets involved in the Gl/S checkpoint. Hepatology 2011). These cells were then co-cultured with LX2 cells (FIG. 1) for 14 days to mimic in vitro the close interactions between CAFs and cancer cells that occur in vivo. The LX2 cells were then separated from the fluorescent cancer cells by FACS, lysed, followed by RNA extraction and qRT-PCR analysis to identify changes in fibroblast miR abundance induced by CCA cancer cells.

We identified significant decreases in multiple fibroblast miRs, including miR-195, miR-192 and miR-126 (FIG. 2). These miRs represent candidate genes involved in the transition from normal fibroblasts to CAFs. We initially focused on the possible role of miR-195 in this process, since earlier studies of fibroblast activation had demonstrated that miR-195 is repressed during the differentiation of quiescent fibroblasts to activated, collagen-producing fibroblasts (Maubach G, Lim M C, Chen J, et al. miR studies in in vitro and in vivo activated hepatic stellate cells. World J Gastroenterol; 17:2748-73; Lakner A M, Steuerwald N M, Walling T L, et al. Inhibitory effects of microRNA 19b in hepatic stellate cell-mediated fibrogenesis. Hepatology; 56:300-10; Chen C, Wu C Q, Zhang Z Q, et al. Loss of expression of miR-335 is implicated in hepatic stellate cell migration and activation. Exp. Cell Res.; 317:1714-25).

Figure 3:
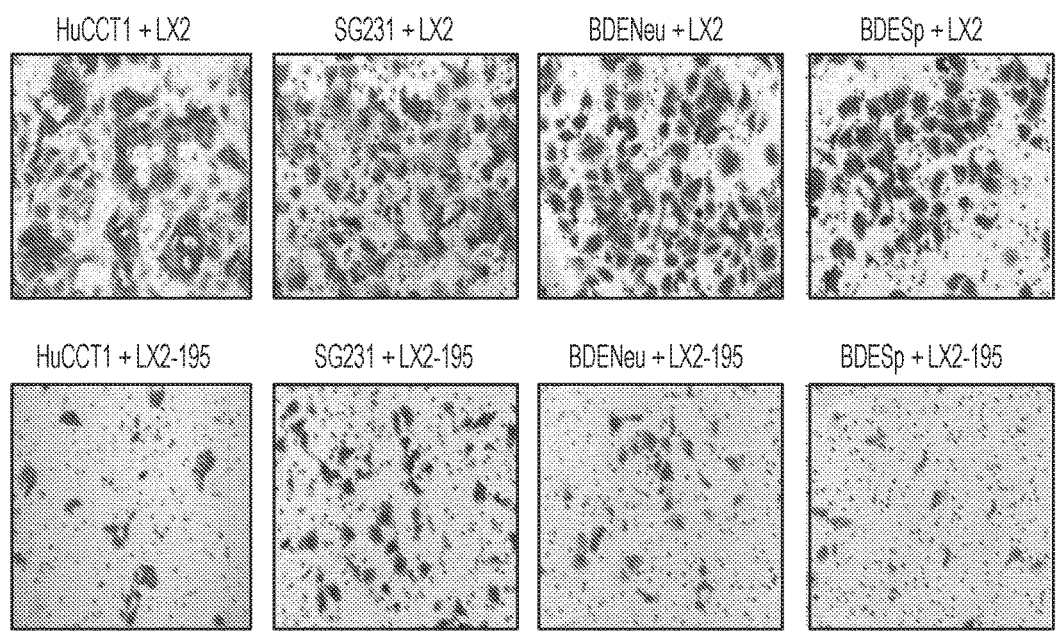
FIG. 3. Restoration of miR-195 in the LX-2 fibroblast-like cell is sufficient to inhibit invasiveness of co-cultured cancer cells. Four different human and rat CCA cells were co-cultured with LX2-NSM or LX2-miR-195 cells. Invading cells were visualized by Crystal Violet staining.

Example 2: Up-Regulation of miR-195 within Fibroblasts is Sufficient to Inhibit Cancer Cell Invasiveness In vitro, CCA cells display significantly higher invasion in a matrigel assay when they are co-cultured with LX2 cells. To determine whether restoring miR-195 expression in LX2 cells had any effect on the invasiveness of co-cultured CCA cells, we generated an LX2 fibroblast cell line (LX2-195) that had restored expression of miR-195, and asked if this had any effect on the behavior of CCA cells in co-culture. Specifically, we co-cultured LX2-195 cells and control LX2 cells (expressing a non-specific inhibitor miR mimic (NSM)) with four different cancer cell lines: HuCCT1, SG231, BDENeu, and BDESp, all of which are intrahepatic CCA cell lines, and then assayed them for cancer cell invasiveness by staining the matrigel with Crystal violet and counting the number of invading cells (neither LX2 control nor LX2-195 cells invade the matrigel). Co-culturing cancer cells with LX2-195 cells resulted in a significant reduction in the invasiveness of all four cancer cell lines examined (FIG. 3). The most parsimonious interpretation of these results is that reversing the reduction of a single miR species in fibroblasts, miR-195, was sufficient to inhibit the invasion of co-cultured cancer cells.

Figure 4:
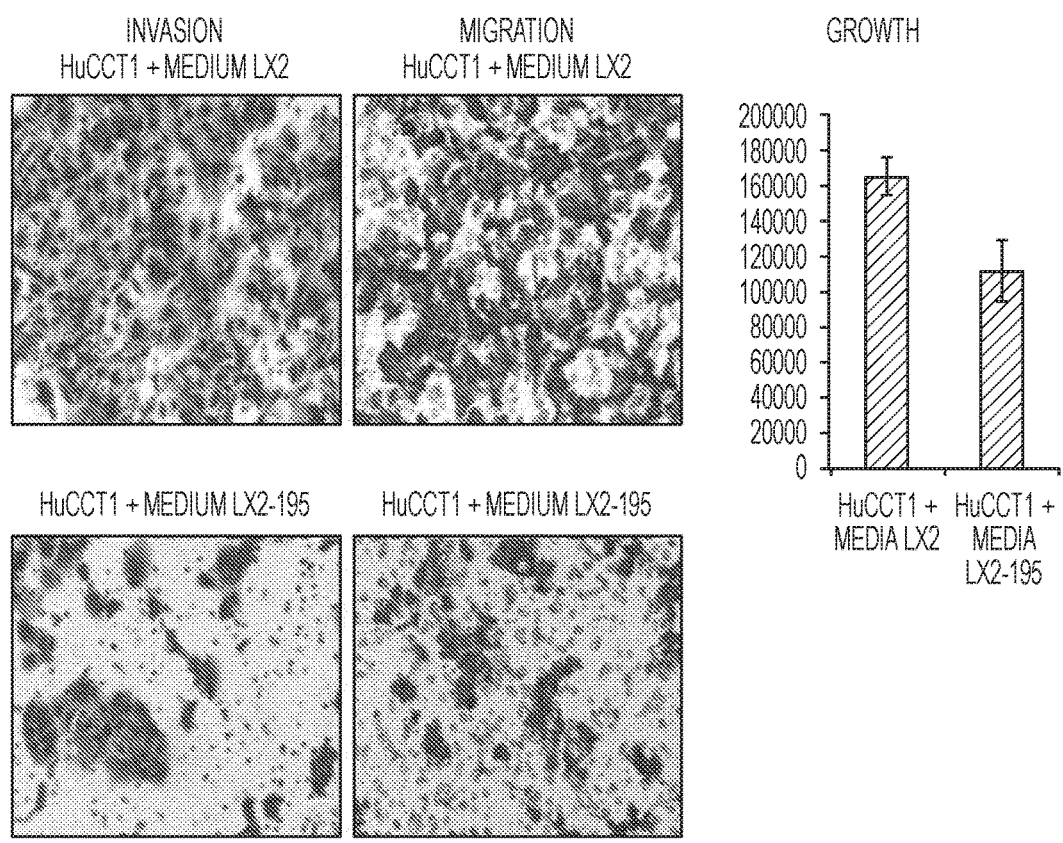
FIG. 4. Up-regulation of miR-195 in fibroblast-like cells inhibits co-cultured cancer cells that were permitted to exchange media, but were not in direct contact. From left to right, the slides demonstrate decreased invasion, migration and growth of cancer cells induced by mediators released in media by LX2-195 cells vs. LX2-control.

Example 3: LX2-195 Cells Release a Diffusible Factor that Inhibits Cancer Cell Invasion, Migration, and Growth The inhibition of cancer cell invasiveness by co-culture with LX2-195 cells (demonstrated above) could be mediated by either direct cell-cell contact and/or by diffusible factors released from LX2-195 cells. Given that diffusible factors have the potential for future therapeutic development, we tested whether LX2-195 cells impacted cancer cell phenotypes in the absence of direct cell-cell contact. In brief, cancer cells and fibroblasts were grown on opposite sides of a transwell apparatus with ~400 nm dia. pores for a period of 5 days (FIG. 4). The cancer cells were then removed and assayed for invasiveness, migration, and growth. Cancer cells exposed to diffusible factors released from LX2-195 cells displayed significant reductions in invasion, migration, and growth, as compared to cancer cells that had been co-cultured with control LX2 cells, which have much lower levels of miR-195.

Figure 5:
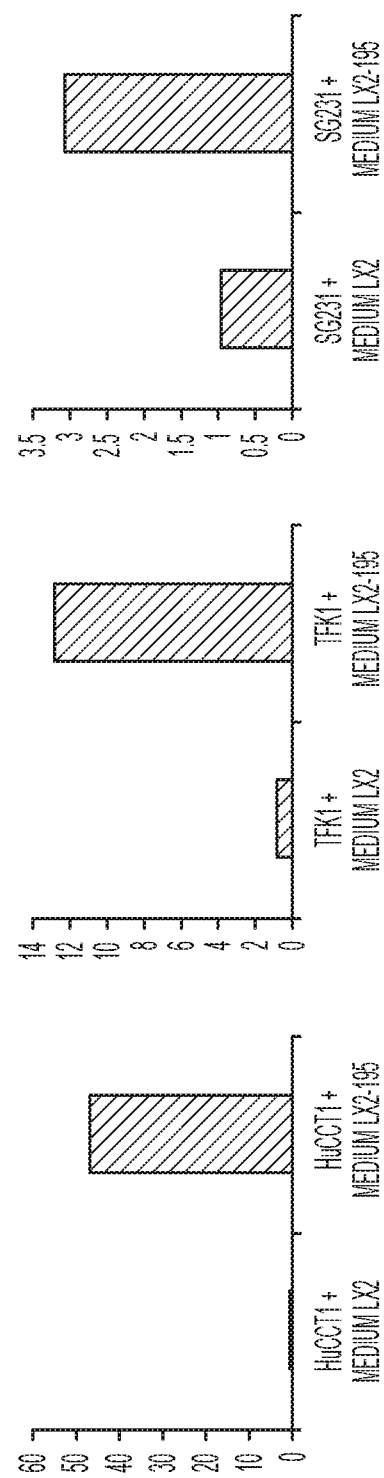
FIG. 5. LX2-miR-195 fibroblast-like cells release soluble factors that cause elevated levels of miR-195 in cancer cells. Levels of miR-195 were measured in three different CCA cancer cells following their exposure to soluble factors from either (left bars) LX2 fibroblasts or (right bars) LX2-195 cells that overexpress miR-195.

Example 4: LX2-195 Cells Release a Diffusible Factor that Causes Up-Regulation of miR-195 in Neighboring Cancer Cells We next tested whether the soluble factors released by LX2-195 cells affected the levels of miR-195 in neighboring cancer cells. Using the transwell assay, cancer cells were exposed to conditioned media from control LX2 or LX2-195 cells. Cancer cells were then purified away from the LX2 cells by FACS, and RNA was extracted from the cancer cells and processed for qRT-PCR to determine the levels of miR-195 and controls. We found that the level of miR-195 in cancer cells was significantly up-regulated following exposure to diffusible factors released by LX2-195 cells (FIG. 5).

Example 5: Fibroblast-like Cells Secrete miR-195 in Extracellular Vesicles (EVs)

Figure 6:
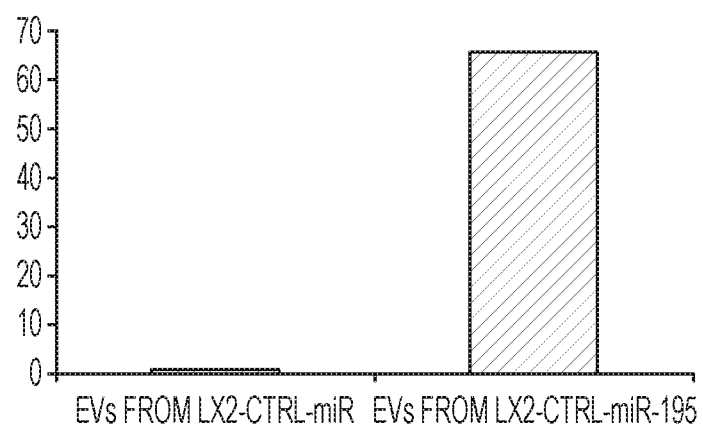
FIG. 6. LX2-miR-195 cells secrete ~60-fold higher levels of miR-195 in exosomes/EVs than control LX2 cells.

To explore the possibility that EVs might contribute to the CAF-cancer interactions outlined in the previous experiments, we asked whether fibroblast-like cells release miR-195 in EVs, and whether the levels of vesicle-associated miR-195 were higher in vesicles released by LX2-195 cells. EVs were collected from the supernatant of control LX2 cells and of LX2-195 cell cultures, followed by RNA extraction and qRT-PCR to determine the relative abundance of miR-195 in the two EV preparations. We observed that control LX2 cells (expressing a non-specific mimic (NSM)) secrete EVs that contain detectable levels of miR-195. However, the levels of miR-195 were >60-fold higher in the in EVs produced by LX2-195 cells (FIG. 6).

Figure 7:
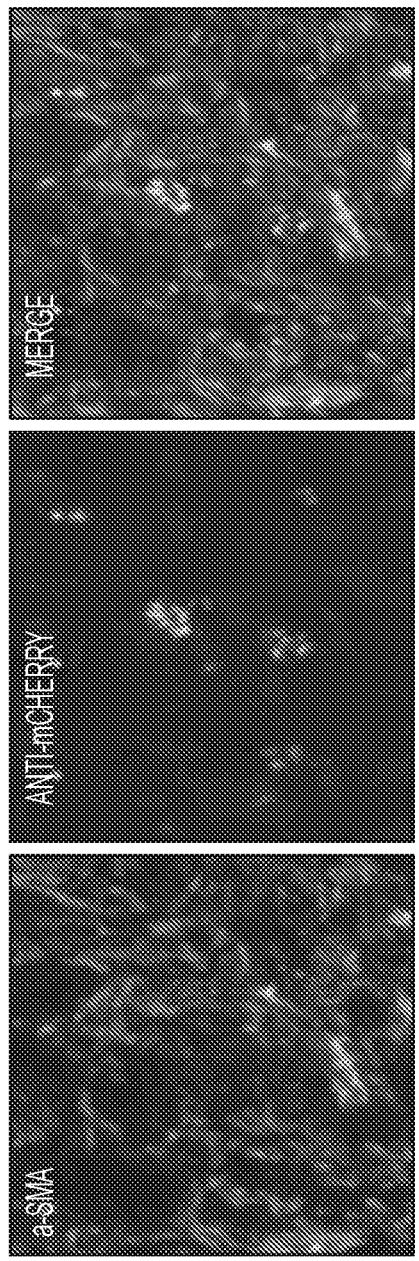
FIG. 7. EVs derived from a hepatic fibroblast-like cell are targeted to CCA cancer cells in vivo., and selectively deliver a protein cargo to the cancer cells but not to surrounding parts of the liver or to other organs of the body. EVs (indicated by the anti-mCherry staining in the figure from the presence of the expression of the TSG101/mCherry fusion protein which is expressed in cells and secreted in EV) are selectively enriched in pockets of the tumor (DAPI stain), that are surrounded by the endogenous fibroblasts (indicated by the α-SMA staining for active fibroblast). EVs are visualized by staining for an EV cargo protein that was expressed in the fibroblast like cells, demonstrating selective delivery of protein to cancer cells in vivo.

Example 6: Fibroblast-like Cell-Derived Extracellular Vesicles (EVs) are Selectively Targeted to Tumor Cells In Vivo The possibility that EVs might contribute to the CAF-cancer signaling observed above, led us to ask whether fibroblast-like cell-derived EVs might be targeted to tumor cells in vivo. To this end, we generated LX2 cells that constitutively express TSG101/mCherry fusion protein (TSG101 is secreted from the cell in EVs (Raposo G, Stoorvogel W. Extracellular vesicles: exosomes, microvesicles, and friends. J Cell Biol 2013; 200:373-83), which allowed us to selectively detect these fibroblasts-derived EVs). EVs from the resulting cell line, LX2-TSG101/mCherry, were collected from the supernatant by standard procedures. The purified, TSG101/mCherry-labeled, fibroblast-derived EVs were then injected into the tail vein of rats, which had been injected with BDEneu tumor cells 24 days earlier and thus had already developed CCA in their liver (we have extensive experience with this model of CCA; see Sirica A E, Zhang Z, Lai G H, et al. A novel "patient-like" model of cholangiocarcinoma progression based on bile duct inoculation of tumorigenic rat cholangiocyte cell lines. Hepatology 2008; 47:1178-90). 24 hours after injection, we sacrificed the rats, removed their livers, lungs, and kidneys, generated slides of these tissues, and processed them for immunofluorescence microscopy using antibodies specific for alpha-Smooth Muscle Actin (stains activated, collagen-producing fibroblasts) and mCherry to detect the fibroblast-derived, TSG101-mCherry-containing exosomes/EVs. These experiments revealed that the fibroblast-derived vesicles were highly enriched in "pockets" of cancer cells within the fibrotic CCA mass in the liver (FIG. 7). We were unable to detect significant staining for TSG101/mCherry in non-cancerous areas of the liver, the lung, or the kidney. These experiments can be carried out using EGFP-containing EVs and tdTomato-expressing cancer cells, and the tissue sections are processed by immunogold label electron microscopy.

Example 7: Fibroblast-like Cell-Derived Extracellular Vesicles (EVs) can Selectively Deliver Heterologous Proteins to Tumor Cells In Vivo EVs from the cell line, LX2-TSG101/mCherry, were collected from the supernatant by standard procedures. The purified, TSG101/mCherry-containing, fibroblast-derived EVs were then injected into the tail vein of rats, which had been injected with BDEneu tumor cells 24 days earlier and thus had already developed CCA in their liver (we have extensive experience with this model of CCA; see Sirica A E, Zhang Z, Lai G H, et al. A novel "patient-like" model of cholangiocarcinoma progression based on bile duct inoculation of tumorigenic rat cholangiocyte cell lines. Hepatology 2008; 47:1178-90). 24 hours after injection, we sacrificed the rats, removed their livers, lungs, and kidneys, generated slides of these tissues, and processed them for immunofluorescence microscopy using antibodies specific for alpha-Smooth Muscle Actin (stains activated, collagen-producing fibroblasts) and mCherry to detect the fibroblast-derived, TSG101-mCherry-containing exosomes/EVs. These experiments revealed that the fibroblast-derived vesicles were highly enriched in "pockets" of cancer cells within the fibrotic CCA mass in the liver (FIG. 7). We were unable to detect significant staining for TSG101/mCherry in non-cancerous areas of the liver, the lung, or the kidney (data not shown). This point is also established by our demonstration that human mammary fibroblast-derived EVs containing an exosomal form of GFP were taken up by human breast cancer cells (FIG. 16).

Figure 8:
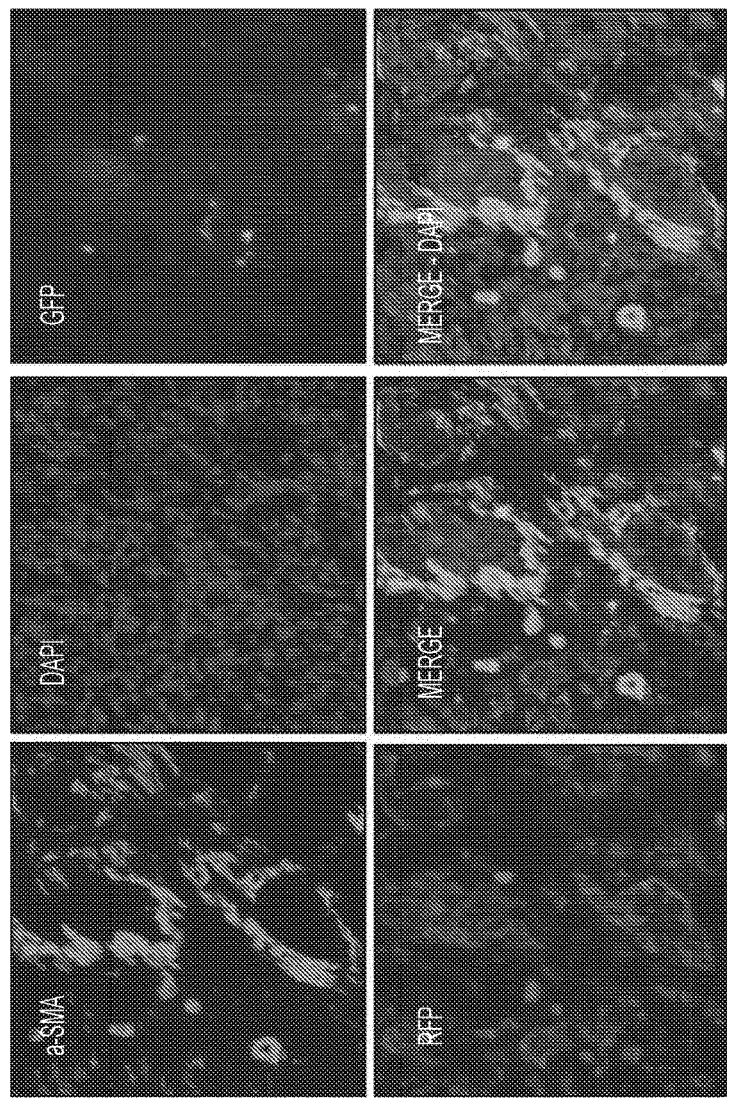
FIG. 8. EV-carried plasmid designed to express Cre recombinase is selectively delivered to rats via tail vein injections. The tumor area was stained with antibodies to detect alpha-SMA (a marker of activated fibroblasts), DAPI (nuclear stain, which detects all cells), and also visualized to detect GFP, which is only expressed if the introduced EVs delivered Cre-expressing DNA into the CCA cells. CCA cells that did not take up functional Cre remained red in these experiments. We observed cords of fibroblasts (stained with anti-alpha SMA), as well as pockets of cancer cells, many of which were expressing GFP, establishing selective delivery of DNA into the cancer cells in vivo.

Example 8: Fibroblast-like Cell-Derived Extracellular Vesicles (EVs) can Selectively Deliver DNA to Tumor Cells In Vivo To further investigate the ability of EVs to selectively deliver cargo molecules to cancer cells, we generated BDEneu cells carrying a Cre-reporter gene, CAG-loxP-tdTomato-loxp-EGFP. These cells display bright red fluorescence due to the expression of tdTomato, (seen as white or light signal emitting cells on black and white drawings using respective optical filters) as but switch from red to green fluorescence following the expression of Cre, which removes the tdTomato gene and places the promoter proximal to the EGFP gene (seen as white or light signal emitting cells on black and white drawings using respective optical filters). These cells were injected into rats, and after tumors were established the rats were treated with a single set of tail vein injections with EVs that had been loaded with a plasmid DNA designed to express Cre recombinase in mammalian cells. As shown in FIG. 8, a significant number of the Cre-reporter CCA cells switched from red to green fluorescence, demonstrating that fibroblast-like cell-derived EVs can deliver DNA to CCA cells in vivo. The fact that some cancer cells retained their original red fluorescence is an outstanding control that points to the efficacy of this assay system for optimizing the variables in the experiment, as well as an internal control to ensure that the correct cells were used. Animals that were not injected with plasmid-loaded EVs failed to produce any green CCA cells. optimize our therapeutic technology.

Figure 9:
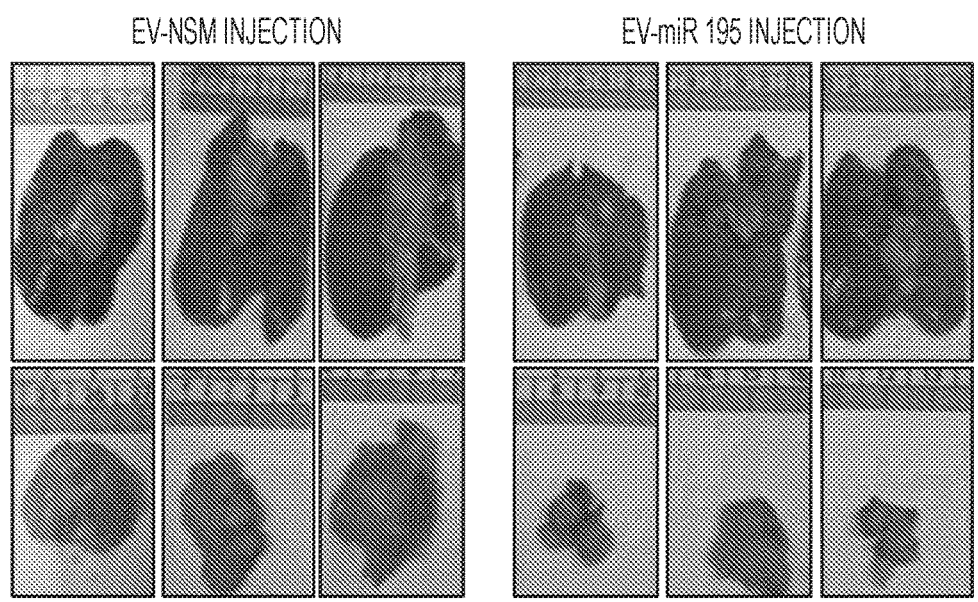
FIG. 9. miR-195-loaded EVs inhibit CCA growth in vivo. EVs were loaded with (left panels) a non-specific miR mimic or (right panels) a miR-195 mimic and injected into rats with CCA. 30 days later, the rats were sacrificed.

Example 9: Fibroblast-Derived, miR-195 Mimic-Loaded EVs Inhibit CCA Growth In Vivo in a Rat Model Taken together, these observations indicate that fibroblast-derived EVs could be used to deliver therapeutic miRs to CCA in vivo. To explore this hypothesis, we collected EVs from the supernatant of LX2 cells, loaded them with a miR-195 mimic by transfection using Lipofectamine RNAiMAX (Invitrogen), and re-purified the loaded EVs by size exclusion chromatography. We also generated control EVs, by transfecting EVs from same LX2 cells with a non-specific miR mimic (NSM). qRT-PCR analysis indicated that miR-195 transfection of vesicles resulted in levels of miR-195 that were ~500,000 times higher than in the control EVs. To determine whether these miR-195-loaded EVs might inhibit CCA growth in vivo, we injected six rats with BDEneu cells, as previously described (Sirica A E, Zhang Z, Lai G H, et al. A novel "patient-like" model of cholangiocarcinoma progression based on bile duct inoculation of tumorigenic rat cholangiocyte cell lines. Hepatology 2008; 47:1178-90). 5 days later, the rats were injected (via tail vein) with either miR-195 mimic-loaded or control miR-loaded EVs (at equivalent numbers of EVs and equivalent dose of miR mimic) Injections were repeated every other day until day 35, at which time the animals were sacrificed and livers were excised. Morphological examination revealed that the tumor size was reduced in all three animals that had been injected with the miR-195 mimic-loaded EVs, relative to the three animals that had been injected with the NSM-loaded EVs (FIGS. 9 and 10). Based on our experience with this animal model, tumor growth in the control-treated animals was similar to what occurs in untreated animals (see Sirica A E, Zhang Z, Lai G H, et al. A novel "patient-like" model of cholangiocarcinoma progression based on bile duct inoculation of tumorigenic rat cholangiocyte cell lines. Hepatology 2008; 47:1178-90).

Example 10: Treatment with miR-195 Loaded EVs Downregulates CDK6 and VEGF (Known Targets of miR-195) in Cancer Cells To test whether miR-195 causes expected changes in gene expression, we measured CDK6 and VEGF mRNA, two reported miR-195 targets (FIG. 11). Both mRNAs were downregulated in all experimental paradigms, including (left panel) direct transfection of BDEneu cells, (middle panel) exposure of cells to conditioned medium of LX2-miR-195, and (right panel) cells incubated with miR-195-loaded EVs.

Example 11: Treatment of Rats with CCA Via Tail Vein with EVs-miR-195 Increases their Survival Significantly We treated 20 cancer-bearing rats with EVs-195 and with EVs-NSM (control), respectively. The treatment was commenced post cancer cell transplantation Day 15 (as to not interfere with the implantation of tumor cells, nor with the early steps of cancer development and growth). Treatment was continued till rats died due to cancer. All experiments had been approved by the Hopkins IACUC. As shown in FIG. 12, rats treated with EVs-195 displayed a statistically significant, 50% increase in survival, providing solid evidence that miR-loaded EVs can have a positive therapeutic effect in vivo.

Example 12: To Identify the Optimal Parameters of miR-195 Loaded EV Therapy in a Rat CCA Model The purpose of the in vivo experiments was to assess if intravenous treatment with EVs loaded with a miR species works in treating CCA. As described herein, we will test several conditions with the purpose of elucidating the rate-limiting factors playing a role in the efficiency of this treatment.

Frequency of treatment: In the preliminary experiments, we have treated rats via tail vein every other day. We now propose to assess if less frequent treatment works equally well. We will do this study on 18 rats, as follows: 6 rats will be the control group (treated as in our preliminary experiments every other day), 6 rats will be treated every 4 days and 6 rats will be treated every 7 days. After 30 days of treatment, all rats will be euthanized and tumors measured.

Timing of treatment: In our preliminary experiments we started treating rats 5 days after BDEneu cancer cell implantation in rat livers. Although not very likely, it is possible that miR-195 delivered by EVs affected tumor implantation in addition to tumor growth. To elucidate this aspect, we will now allow the tumors to develop for 2 weeks, then the treatment with miR-195-EVs will commence. We chose 2 weeks because, from our previous experiments, we know that these rats have tumors developed already by week 2, and some of them die of cancer at week 4. We will compare the treatment efficiency with the control arm from the experiment above. For this experiment we will require 6 rats.

miR dose and EV dose: For preliminary experiments, for each rat, we utilized 200 μg miR mimic to transfect 200 μg of EVs (based on protein weight, ratio 1:1) before delivering in vivo. However, we would like to test if a different miR dose or different EV dose is more efficient in treating CCA or, if the efficiency is maintained while decreasing the dose (with the purpose of cost saving). First, we will perform an in vitro experiment to determine the best miR to EV ratio. We propose to utilize miR to transfect EVs in a weight ratio of 0.5:1, 1:1, 2:2 and 4:1. Next, we will utilize these transfected EVs to treat HuCCT1 cells in vitro and then determine by qRT-PCR the level of miR upregulation as a function of miR quantity used to transfect EVs. We utilize a concentration of miR mimic of 15 μg per μL. We measure the amount of exosomes based on the weight of the protein content. We usually extract approximately 30 μg of exosomes from one 150 cm cell culture dish. Next, we will utilize the weight ratio miR:EVs that was determined in vitro for all following experiments. We will then vary the amount of miR delivered per rat (with the associated quantity of EVs). We will have 4 experimental arms: 50 μg of miR mimic per injection/rat, 100 μg, 200 μg and 400 μg. Each experimental arm will include 6 rats for a total of 24 rats. We will keep all other parameters of the experiments constant as in our preliminary experiments presented above (injection timing-5 days post-cancer implantation and injections every other day).

Kaplan-Meyer curves/survival: Once the optimal frequency, timing and dose of the treatment is established, we will perform an experiment to determine the survival of rats treated with EV-miR-195. The control arm will include 12 rats treated with EV-NSM (negative control, EVs transfected with control miR) and the treatment arm will include 12 rats treated with EV-miR195. We will record the date of death and therefore be able to perform Kaplan-Meyer curves. These experiments will offer valuable information from a clinical perspective, as the size of the tumor is important, however, survival is also of utmost importance. While we have already demonstrated that EV injections can prolong survival (FIG. 11), survival studies will remain a key endpoint as we strive to develop an effective anti-cancer therapy based on miR-loaded EVs.

Example 13: To Characterize the CCA Phenotype Induced by EVs Loaded with miR-126, and -192, Respectively miR-126 and -192 were among the top 3 candidate miRs in our screen. In fact, miR-126 and -192 were more strongly depleted in response to CCA cells than miR-195. We will pursue the same sets of experiments on miR-126 and miR-192 that we have performed and proposed for miR-195. For example, we will generate LX2 cells that express miR-126, and cells that express miR-192, and compare the effect that these cells have on the neoplastic properties of co-cultured CCA cells, relative to control LX2 cells expressing a non-specific mimic (NSM)), both in direct co-culture assays and in transwell co-culture assays. In fact, we have already generated a LX2-126 line, and our initial experiments indicates that LX2-126 cells inhibit CCA invasiveness (FIG. 13). FIG. 13 shows LX2 cells expressing miR-126 inhibit CCA invasiveness in vitro. HuCCT1 cells were co-cultured directly with LX2 cells expressing either (upper image) a control miR, or (lower image) miR-126. Invasiveness of HuCCT1 cells was decreased 3.2 fold when co-cultured with LX2-126 cells.

In addition, the LX2-126 cells appeared to inhibit CCA migration in a scratch assay test (FIG. 14). FIG. 14 shows LX2 cells expressing miR-126 inhibit CCA migration 4-fold in vitro. HuCCT1 cells were co-cultured directly with LX2 cells expressing either a controls miR or miR-126. Migration was measured in a scratch assay.

As we move forward with these studies, from cells to miR-loaded EVs, and from in vitro experiments to in vivo experiments, we will also incorporate similar controls as those outlined previously, including characterization of miR-loaded EVs (by immunoEm, differential centrifugation & immunoblot, etc.).

As for the in vivo experiments, they will mirror those shown and proposed for miR-195-loaded EVs. Specifically, we will inject miR-loaded EVs into the tail vein of rats that were previously induced to develop iCCA. We will next determine differences in size of tumors in the treatment vs. control arm. We will also perform experiments to determine the optimal dose of EVs, miR loaded into EVs, the duration of treatment, frequency of injections and finally derive Kaplan-Meyer curves to indicate if there is a change in survival of rats treated with EV-miRs by tail vein. To determine the molecular & cellular impact of treatment with EV-loaded miR-126 and -192, we will perform experiments as outlined under Aim 1a. In brief, we will collect CCA cells (in vivo experiments and in vitro culture), extract RNA, measure the levels of known miR-126 and miR-192 targets, perform RNA-seq, followed by pathway analyses, and follow-on experiments to identify the mechanisms by which injected EVs inhibit cancer growth (if they do).

Example 14: Delivery of a Small Molecule to Cancer Cells

MDA-MB-231 breast cancer cells (red) were incubated with EVs obtained from human mammary fibroblast cells that had been incubated previously with the exosomal lipid N-F-PE. These EVs were taken up by the breast cancer cells, demonstrating that fibroblast-like cell-derived EVs can be loaded with small molecules and selectively deliver the small molecules to cancer cells The results reported herein above were carried out using the following methods and materials.

Cell Culture

LX2 is a human liver stellate cell line derived to study fibrogenesis. HuCCT1 was derived from a patient with a moderately differentiated adenocarcinoma of the intrahepatic biliary tree HuCCT1 was established from a patient with moderately differentiated adenocarcinoma of the intrahepatic biliary tree. SG231 is a cholangiocarcinoma cell line derived as described 41. TFK1 is an extrahepatic CCA cell line. BDENeu and BDEsp are rat intrahepatic CCA cell lines derived as described.RGF is a rat portal fibroblast cell line established by Fausther et al 21, 22. H69, a gift from Dr. Jefferson (Tufts University, Boston, Mass.), are normal human intrahepatic cholangiocytes derived from a normal liver prior to liver transplantation. All cell lines were maintained and grown as described previously.

EVs Preparation and Characterization

EVs were separated via ultracentrifugation as described before from LX2 cell culture medium that had been cultured for 72 hours with EV free FBS. Multi-parameter nanoparticle optical analysis (Nanosight) and Transmission Electron Microscope (TEM) were utilized to determine the shape, size and tracking the brownian movement of EVs. Western blot for EV-specific proteins was performed with anti-CD63 antibody (Santa Cruz Dallas, Tex.) and anti-TSG-101 antibody (Abcam Cambridge, Mass.) as described before.

miRNA Mimic Loading of EVs

Lipofectamine RNAiMAX (Life Technologies, NY) was used to transfect miR mimic into EVs with an adjusted protocol according to manufacturer's instruction. MiR-195 mimic and NSM were purchased from Dharmacon GE Healthcare. Then free miR-195 mimics were isolated with a micropartition system (Vivaspin 2, 50 kDa MWCO PES, GE Healthcare, Laurel, Md.). The mixed suspension was added into the filter and centrifuged at 1500 g for 5 min, the supernatant collected and either placed on the top of cells for in vitro experiments or used to inject into the CCA rat model in the in vivo experiments.

RNA Extraction

RNA from EVs was extracted by a modified Trizol method while spiking in cel-miR-39 during the lysis step. Cells were lysed with Trizol reagent (Invitrogen, Carlsbad, Calif.) according to the manufacture's protocol.

MicroRNA Real Time PCR Array

LX2 and HuCCT1 MIEG3-EGFP were seeded at same amounts in flasks, then directly co-cultured for 14 days, EGFP-negative cells were sorted and collected by FACS, followed by RNA extraction. 100 μg RNA were used for RT-PCR array for co-cultured LX2 cells with LX2 cultured alone as control. Following analysis, select miRs that were down-regulated in co-cultured LX2 cells were selected for follow-up experiments.

Quantitative RT-PCR (qRT-PCR) for miRs Expression.

qRT-PCR was performed to detect the miR-195 expression in EVs, CCA cell lines, and CCA tumor mass cells. For miR-195 expression in EVs, we used cel-miR-39 as control, while for miR-195 expression in cells, RNU6B was used to normalize the data as described before.

qRT-PCR for mRNA Expression.

RNA was reversed transcribed according to the manufacture protocol (Thermo Scientific), IQ SYBR Green Supermix (Bio-Rad, Hercules, Calif.) was for used real time PCR amplification, GAPDH was used to normalize mRNA expression level, and melting curve analysis was used to confirm the PCR results.

Plasmids, Transfection and Lentivirus/retrovirus Infection

Vectors were purchased from Addgene (Cambridge, Mass.). Viral supernatants were produced by transfection of HEK-293T cells with a packaging plasmid (pVSV-G). BDEneu cells were infected with viral supernatant with Polybrene at a final concentration of 8 μg/ul. pCDH1-EF1-mCherry-TSG101-IRES-GFP was used to infecft LX2 cells. GFP positive cells were sorted and used to isolate EVs with mCherry on the surface. pMSCV-loxp-dsRed-loxp-eGFP-Puro-WPRE was used as above to produce viral particles, that were then used to infect BDEneu cells. Puromycin was used to select for stably infected cells. When a Cre-recombinase encoding plasmid is detected, cells switch color from RFP to GFP after excision of the loxp-dsRed-loxP element.

Conditioned Media Preparation

Confluent LX2-miR-195 mimic/NSM cells were incubated with DMEM supplemented with penicillin/streptomycin, 0% FBS. Three days later, the conditioned media was collected, filtered, and used immediately.

Cell Invasion/migration Assay

Cell invasion assays were performed using invasion chambers (Cat#354480, Corning, Tewksbury, Mass.) while for cell migration assays 8 μm Transwell plates (Cat#3422, Corning, Tewksbury, Mass.) were used. For both assays, DMEM with 10% FBS was placed in the lower chamber as chemoattractant. For directed transfection of CCA lines, 2 days after transfection, $3 \times 10^4$ were seed into invasion chamber. For co-culture invasion assay, either $3 \times 10^4$ HuCCT1, BDEneu, SG231 or BDEsp were co-cultured with $3 \times 10^4$ LX2-NSM or LX2-miR-195 mimc cells or RGF-NSM/miR-195 mimic at 37° C. for 2 days, then $6 \times 10^4$ cells were diluted in serum-free medium and placed into the upper chambers. After 48 hours the non-invading/non-migrating cells were removed from the membrane upper surface with cotton swabs, and invaded/migrated cells on the lower side of chamber were stained with crystal violet. Cells were counted in 3 random fields at a magnification of 200×.

Proliferation of CCA Cell Lines Co-cultured with LX2/RGF miR-195 Mimic/NSM, and CCA Cell Lines Directly Transfected with miR-195 Mimic/NSM LX2 or RGF cells transfected with miR-195 mimic or NSM were cultured for 2 days, then washed and trypsinised, centrifuged and washed 3 times with PBS. After cell counting, $5 \times 10^4$ LX2 or RGF cells were seeded into the upper well of 12 well 0.4 μm transwell co-culture system (cat#3460, Corning, Tewksbury, Mass.). For the bottom chamber, $1 \times 10^5$ CCA cells (BDEneu, HuCCT1) were seeded at the same time after trypinization and counting as above. After 5 days, the CCA cell number was determined by counting. For directly transfected BDEneu and HuCCT1 with miR-195 mimic or NSM, 1000 cells were seeded into 96 well plates, MTs Assay (CellTiter 96 Aqueous One solution Cell Proliferation Assay Cat# G3580, Promega Corporation, Sunnyvale, Calif.) was used to determine the proliferation.

Animal Studies

Fischer 344 male (150-170 g) were purchased from Harlan (Frederick, Md.) and housed in the animal facility at Johns Hopkins University. All animal work was approved by and conducted in accordance with the guidelines of the Institutional Animal Care and Use Committee at the Johns Hopkins University. For the CCA rat model Fischer 344 male rats were anesthetized and then inoculated with $1 \times 10^6$ BDEneu cells in 100 μl HBSS injected into the left liver lobe, followed by ligation of the common bile duct. Rats were monitored daily until day 5 or day 15, when the treatment with miR-loaded EVs started.

Treatment of CCA Rats with miR-195-loaded EVs

Initially 6 CCA rats were randomized into 2 groups. Starting at day 5, the rats received EV loaded with miR-195 mimic/NSM via tail veil injections every 2 days. After 25 days, rats were sacrificed, tumor weight and size were measured, and tissue specimen frozen in O.C.T. compound. Tissue sections were stained with primary antibodies and detected using Alexa Fluor dye-conjugated secondary antibodies. Microphotographs were obtained using a Zeiss laser scanning microscope (LSM 510). In addition, single cell suspension from tumor masses were used to sort the BDEneu cells with RFP fluorescence. MiR-195 levels in miR-195 treated rats and NSM treated controls were measured via RT-PCR.

Kaplan-Meyer Survival Curves

In a follow up animal in vivo experiment, 20 CCA rats were randomized in a control group of 9 CCA rats treated with NSM and a treatment group of 11 rats, treated with miR-195 mimic, both starting from Day 15 Animals were monitored daily and the date of death of each rat recorded and the data incorporated into a Kaplan-Meyer curve. Data were analyzed with the log-rank (Mantel-Cox) test.

Detection of the Location of EVs in CCA Mass of Liver

Isolated EVs from LX2-pCDH1-EF1-mCherry-TSG101-IRES-GFP cells were injected into tail veins of CCA rats. After 24 hours the rats were sacrificed and tissue specimen of the tumor mass were frozen in O.C.T. compound. Tissue sections were stained with primary antibodies against mCherry (cat#632496 Clontech, Mountain View, Calif.) and alpha-SMA (cat# A2547, Sigma-Aldrich, St. Louis, Mo.) to detect the injected EVs and to measure the degree of the fibrotic change in the tumor mass. Furthermore, BDEneu cells infected with pMSCV-loxp-dsRed-loxp-eGFP-Puro-WPRE lentiviral construct were injected into rat livers as described above to generate the CCA model, and after 20 days, EVs transfected with Cre plasmid were administered to the rats via tail veil injections. 4-6 days later, rats were sacrificed and tumor sections obtained as described above. Cells that switched color from dsRed to EGFP indicate BDEneu tumor cells that have taken up EVs loaded with Cre-recombinase plasmid.

Proliferation and Apoptosis Measurement In Vivo

Tumor mass specimens were embedded in paraffin, sections were stained with primary antibody Ki67 (cat#550609, BD San Jose, Calif.), caspase 3 (cat#96615, Cell Signaling Technology, Dancers, Mass.), alpha-SMA and TUNEL in situ cell death fluorescein (Sigma-Aldrich, St. Louis, Mo.) to determine the levels of proliferation, apoptosis, as well as fibrotic infiltrate. Image J was used to identify the florescence intensity.

Other Embodiments

From the foregoing description, it will be apparent that variations and modifications may be made to the invention described herein to adopt it to various usages and conditions. Such embodiments are also within the scope of the following claims.

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

All patents and publications mentioned in this specification are herein incorporated by reference to the same extent as if each independent patent and publication was specifically and individually indicated to be incorporated by reference.

What is claimed is:

1. An extracellular vesicle isolated from a liver cancer associated fibroblast (CAF), wherein the vesicle comprises an exogenous agent, wherein the exogenous agent is a heterologous polynucleotide comprising miR-195, miR-126, or miR-192 whose expression has been identified as being down-regulated in the CAF.

2. The extracellular vesicle of claim 1, wherein the extracellular vesicle selectively targets a cancer cell.

3. The extracellular vesicle of claim 1, wherein the polynucleotide is a recombinant polynucleotide heterologously expressed in the CAF or loaded into the CAF or extracellular vesicle ex vivo.

4. The extracellular vesicle of claim 1, wherein the vesicle expresses increased levels of one or more markers selected from the group consisting of alpha-SMA, Collagen, Vimentin (FSP-1), SlOO, Metalloproteinases, NG2, PDGFR-B, SDF1/CXCL12, CD34, Fibroblast activation protein (FAP), FSP-1, CD31, Thy-1, and Gremlin or expresses reduced levels of laminin.

5. The extracellular vesicle of claim 1, wherein the CAF expresses one or more of alpha smooth muscle actin and/or collagen.

6. The extracellular vesicle of claim 1, wherein the vesicle expresses reduced levels of laminin.

7. The extracellular vesicle of claim 1, wherein the CAF is derived from a fibroblast cultured for at least 1-14 days in the presence of a cancer cell or in the presence of conditioned media derived from a cancer cell culture.

8. A pharmaceutical composition comprising the vesicle of claim 1.

9. A method for obtaining the extracellular vesicle of claim 1, the method comprising culturing a fibroblast or stromal cell in conditioned media obtained from a cancer cell culture, and isolating extracellular vesicles from the media.

10. An extracellular vesicle produced according to the method of claim 9.

11. A method of delivering a polynucleotide to a cell, the method comprising contacting the cell with the extracellular vesicle of claim 1, thereby delivering the polynucleotide to the cell.

12. A method of altering gene expression in a cell, the method comprising contacting the cell with the extracellular vesicle of claim 1.

13. A method for treating cancer in a subject comprising administering to the subject a pharmaceutical composition comprising an effective amount of the extracellular vesicle of claim 1.

14. The method of claim 13, wherein the cancer is a liver cancer.

15. An extracellular vesicle isolated from a cholangiocarcinoma, hepatocellular carcinoma, or hepatoma cancer associated fibroblast (CAF), wherein the vesicle comprises an exogenous agent, wherein the exogenous agent is a heterologous polynucleotide comprising miR-195, miR-126, or miR-192 whose expression has been identified as being down-regulated in the CAF.

16. The extracellular vesicle of claim 15, wherein the extracellular vesicle selectively targets a cancer cell.

17. The extracellular vesicle of claim 15, wherein the polynucleotide is a recombinant polynucleotide heterologously expressed in the CAF or loaded into the CAF or extracellular vesicle ex vivo.

18. The extracellular vesicle of claim 15, wherein the vesicle expresses increased levels of one or more markers selected from the group consisting of alpha-SMA, Collagen, Vimentin (FSP-1), SlOO, Metalloproteinases, NG2, PDGFR-B, SDF1/CXCL12, CD34, Fibroblast activation protein (FAP), FSP-1, CD31, Thy-1, and Gremlin or expresses reduced levels of laminin.

19. The extracellular vesicle of claim 15, wherein the CAF expresses one or more of alpha smooth muscle actin and/or collagen.

20. The extracellular vesicle of claim 15, wherein the vesicle expresses reduced levels of laminin.

21. The extracellular vesicle of claim 15, wherein the CAF is derived from a fibroblast cultured for at least 1-14 days in the presence of a cancer cell or in the presence of conditioned media derived from a cancer cell culture.

22. A pharmaceutical composition comprising the extracellular vesicle of claim 15.

23. A method for obtaining the extracellular vesicle of claim 15, the method comprising culturing a fibroblast or stromal cell in conditioned media obtained from a cancer cell culture, and isolating extracellular vesicles from the media.

24. An extracellular vesicle produced according to the method of claim 23.

25. A method of delivering a polynucleotide to a cell, the method comprising contacting the cell with the extracellular vesicle of claim 15, thereby delivering the polynucleotide to the cell.

26. A method of altering gene expression in a cell, the method comprising contacting the cell with the extracellular vesicle of claim 15.

27. A method for treating cancer in a subject comprising administering to the subject a pharmaceutical composition comprising an effective amount of the extracellular vesicle of claim 15.

28. The method of claim 27, wherein the cancer is cholangiocarcinoma, hepatocellular carcinoma, or hepatoma.

* * * * *